US010610299B2

(12) United States Patent
Rueber et al.

(10) Patent No.: US 10,610,299 B2
(45) Date of Patent: Apr. 7, 2020

(54) TECHNIQUE FOR GENERATING A BONE PLATE DESIGN

(75) Inventors: Jens Rueber, Freiburg (DE); Reinhard Koehler, Freiburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 917 days.

(21) Appl. No.: 14/364,867

(22) PCT Filed: Dec. 14, 2011

(86) PCT No.: PCT/EP2011/006314
§ 371 (c)(1),
(2), (4) Date: Sep. 9, 2014

(87) PCT Pub. No.: WO2013/087082
PCT Pub. Date: Jun. 20, 2013

(65) Prior Publication Data
US 2015/0051876 A1 Feb. 19, 2015

(51) Int. Cl.
*G06F 17/50* (2006.01)
*A61B 34/10* (2016.01)
*G06T 19/20* (2011.01)
*A61B 17/80* (2006.01)

(52) U.S. Cl.
CPC .............. *A61B 34/10* (2016.02); *A61B 17/80* (2013.01); *G06F 17/50* (2013.01); *G06T 19/20* (2013.01); *A61B 2034/105* (2016.02); *G06T 2219/2021* (2013.01)

(58) Field of Classification Search
CPC ...................................................... G06F 17/50

USPC ............................................................ 703/1
See application file for complete search history.

(56) References Cited

U.S. PATENT DOCUMENTS

| 4,436,684 | A | 3/1984 | White |
| 4,976,737 | A | 12/1990 | Leake |
| 5,360,446 | A | 11/1994 | Kennedy |
| 5,365,996 | A | 11/1994 | Crook |

(Continued)

FOREIGN PATENT DOCUMENTS

| DE | 10003533 A1 | 8/2001 |
| JP | 2001092950 A | 4/2001 |

(Continued)

OTHER PUBLICATIONS

Diego L. Fernandez, Correction of Post-Traumatic Wrist Deformity in Adults by Osteotomy, Bone-Grafting, and Internal Fixation. (Year: 1982).*

(Continued)

*Primary Examiner* — Lechi Truong
(74) *Attorney, Agent, or Firm* — Lerner, David, Littenberg, Krumholz & Mentlik, LLP

(57) ABSTRACT

A computer-implemented technique for generating a data set that geometrically defines a bone plate design is presented. A method implementation of this technique comprises visualizing, based on shape data of a bone, a bone model on a display device, deriving, responsive to a user interaction signal that is indicative of a user interaction relative to the bone model, plate design data representative of a plate-specific design property, and generating a data set that geometrically defines a bone plate design from at least the plate design data and one or more generic plate parameters.

18 Claims, 16 Drawing Sheets

(56) References Cited

U.S. PATENT DOCUMENTS

| | | | |
|---|---|---|---|
| 5,741,215 A | 4/1998 | D'Urso | |
| 5,798,924 A | 8/1998 | Eufinger et al. | |
| 5,880,962 A | 3/1999 | Andersson et al. | |
| 5,964,761 A | 10/1999 | Kambin | |
| 6,293,950 B1* | 9/2001 | Lynch | A61B 17/8605 411/5 |
| 6,327,491 B1 | 12/2001 | Franklin et al. | |
| 6,423,068 B1 | 7/2002 | Reisberg et al. | |
| 6,645,250 B2 | 11/2003 | Schulter | |
| 6,648,640 B2 | 11/2003 | Rubbert et al. | |
| 6,738,657 B1 | 5/2004 | Franklin et al. | |
| 6,772,026 B2 | 8/2004 | Bradbury et al. | |
| 6,786,930 B2 | 9/2004 | Biscup | |
| 6,846,179 B2 | 1/2005 | Chapouland et al. | |
| 6,915,178 B2 | 7/2005 | O'Brien et al. | |
| 6,932,842 B1 | 8/2005 | Litschko et al. | |
| 6,978,188 B1 | 12/2005 | Christensen | |
| 7,113,841 B2 | 9/2006 | Abe et al. | |
| 7,117,027 B2 | 10/2006 | Zheng et al. | |
| 7,383,163 B2 | 6/2008 | Holberg | |
| 7,388,972 B2 | 6/2008 | Kitson | |
| 7,463,942 B2 | 12/2008 | O'Brien et al. | |
| 7,491,180 B2 | 2/2009 | Pacheco | |
| 7,603,192 B2 | 10/2009 | Martin et al. | |
| 7,621,744 B2 | 11/2009 | Massoud | |
| 7,636,459 B2 | 12/2009 | Dore et al. | |
| 7,693,192 B2 | 4/2010 | Adachi et al. | |
| 7,702,380 B1 | 4/2010 | Dean | |
| 7,747,305 B2 | 6/2010 | Dean et al. | |
| 7,887,327 B2 | 2/2011 | Marotta | |
| 7,909,610 B1 | 3/2011 | Amato | |
| 7,967,868 B2 | 6/2011 | White et al. | |
| 7,981,158 B2 | 7/2011 | Fitz et al. | |
| 8,010,180 B2* | 8/2011 | Quaid | 600/424 |
| 8,014,984 B2 | 9/2011 | Iannotti et al. | |
| 8,055,487 B2 | 11/2011 | James | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,078,255 B2 | 12/2011 | Bhandarkar et al. | |
| 8,083,745 B2 | 12/2011 | Lang et al. | |
| 8,092,465 B2 | 1/2012 | Metzger et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,166,627 B2 | 5/2012 | Deffrennes | |
| 8,170,641 B2 | 5/2012 | Belcher | |
| 8,200,355 B2 | 6/2012 | Lee et al. | |
| 8,246,680 B2* | 8/2012 | Betz | A61F 2/30942 606/130 |
| 8,435,270 B2 | 5/2013 | Furrer et al. | |
| 8,484,001 B2 | 7/2013 | Glozman et al. | |
| 8,617,171 B2* | 12/2013 | Park | G06T 7/0012 606/88 |
| 8,650,005 B2 | 2/2014 | Liao | |
| 9,066,733 B2 | 6/2015 | Furrer et al. | |
| 9,277,948 B2 | 3/2016 | Furrer et al. | |
| 9,317,634 B2 | 4/2016 | Davison et al. | |
| 9,381,072 B2 | 7/2016 | Furrer et al. | |
| 2002/0028980 A1* | 3/2002 | Thierfelder | A61B 17/00234 600/37 |
| 2003/0083750 A1 | 5/2003 | Schulter | |
| 2003/0109784 A1 | 6/2003 | Loh et al. | |
| 2004/0006125 A1* | 1/2004 | Remington | A61L 27/56 514/423 |
| 2004/0102866 A1 | 5/2004 | Harris et al. | |
| 2004/0117015 A1 | 6/2004 | Biscup | |
| 2004/0265770 A1 | 12/2004 | Chapoulaud et al. | |
| 2005/0059873 A1 | 3/2005 | Glozman et al. | |
| 2005/0085817 A1 | 4/2005 | Ringeisen | |
| 2006/0085000 A1* | 4/2006 | Mohr | A61B 17/8076 606/281 |
| 2006/0217813 A1 | 9/2006 | Posnick et al. | |
| 2006/0224242 A1 | 10/2006 | Swords et al. | |
| 2006/0241388 A1 | 10/2006 | Lavallee | |
| 2007/0238069 A1 | 10/2007 | Lovald et al. | |
| 2008/0154120 A1* | 6/2008 | von Jako | A61B 5/06 600/411 |
| 2008/0195240 A1 | 8/2008 | Martin et al. | |
| 2008/0234754 A1 | 9/2008 | McCarthy et al. | |
| 2008/0257363 A1 | 10/2008 | Schoenefeld et al. | |
| 2009/0130942 A1* | 5/2009 | Post | A41G 7/00 446/27 |
| 2009/0149977 A1 | 6/2009 | Schendel | |
| 2009/0222102 A1 | 9/2009 | Deffrennes | |
| 2009/0226068 A1 | 9/2009 | Fitz et al. | |
| 2010/0106463 A1 | 4/2010 | Hindman et al. | |
| 2010/0145231 A1* | 6/2010 | Takahashi | A61B 5/1075 600/587 |
| 2010/0152782 A1 | 6/2010 | Stone et al. | |
| 2010/0262193 A1 | 10/2010 | Frigg et al. | |
| 2010/0292963 A1 | 11/2010 | Schroeder | |
| 2011/0032184 A1* | 2/2011 | Roche | G06F 3/011 345/156 |
| 2011/0066245 A1 | 3/2011 | Lang et al. | |
| 2011/0070562 A1 | 3/2011 | O'Brien et al. | |
| 2011/0269100 A1 | 11/2011 | Furrer et al. | |
| 2011/0301609 A1 | 12/2011 | Longepied | |
| 2012/0010711 A1 | 1/2012 | Antonyshyn et al. | |
| 2012/0029574 A1 | 2/2012 | Furrer et al. | |
| 2012/0123577 A1 | 5/2012 | Chapoulaud et al. | |
| 2012/0215227 A1* | 8/2012 | Fitzpatrick | A61B 17/14 606/87 |
| 2012/0259592 A1 | 10/2012 | Liao | |
| 2013/0094732 A1* | 4/2013 | Chabanas | G06K 9/6205 382/128 |
| 2014/0081121 A1* | 3/2014 | Wilhelm | A61B 17/80 600/409 |

FOREIGN PATENT DOCUMENTS

| | | |
|---|---|---|
| WO | 0156491 A2 | 8/2001 |
| WO | 03030787 A1 | 4/2003 |
| WO | 2006125652 A1 | 11/2006 |

OTHER PUBLICATIONS

Daniela Serban: Integrated Design to Manufacturing Process of Customised Maxillofacial Prostheses, Galway Mayo Institute of Technology, 2004, Retrieved from the Internet: URL:http:l/cua.openrepository.com/cua/bitstream/10759/313774/1/ Daniela_Serban_20130917143005.pdf.

European Examination Report for Application No. 11796633.3 dated Aug. 6, 2015.

Dérand et al., "Virtual Bending of Mandibular Reconstruction Plates Using a Computer-Aided Design", J Oral Maxillofac Surg, 2009, pp. 1640-1643.

Pro/SHEETMETAL, XP007901024, 126 pages.

Synthes, "Compact 2.4 UniLOCK: Reconstruction system for the mandible", Technique Guide, copyright 2007, XP-002690160.

Wilde et al., "Mandible reconstruction with patient-specific pre-bent reconstruction plates; comparison of a transfer key method to the standard method—results of an in vitro study", Int J CARS (2012) 7:57-63.

Bryan Bell R et al: "Computer Planning and Intraoperative Navigation for Palatomaxillary and Mandibular Reconstruction With Fibular Free Flaps", Journal of Oral and Maxillofacial Surgery, vol. 69. No. 3., Feb. 3, 2011, pp. 724-732.

Lovald S et al: "Biomechanical Optimization of Bone Plates Used in Rigid Fixation of Mandibular Symphysis Fractures", Journal of Oral and Maxillofacial Surgery, Saunders, Philadelphia, PA, US, vol. 68, No. 8, Aug. 1, 2010, pp. 1833-1841.

Mazzoli A et al: "Direct fabrication through electron beam melting technology of custom cranial implants designed in a PHANToM-based haptic environment", Materials and Design, London, GB, vol. 30. No. 8., Sep. 1, 2009, pp. 3186-3192.

(56) References Cited

OTHER PUBLICATIONS

Partial International Search Report for Application No. PCT/EP2011/006314 dated Oct. 10, 2012.
Sekou Singare et al: "Fabrication of customised maxillo-facial prosthesis using computer-aided design and rapid prototyping techniques", Rapid Prototyping Journal Emerald UK, vol. 12, No. 4, 2006, pp. 206-213.
Bai et al., "CAD/CAM Surface templates as an alternative to the intermediate wafter in orthognathic surgery", Oral Surgery, Oral Medicine, Oral Pathology, Oral Radiology, and Endodontology, vol. 110, Issue 5, pp. e1-e7, Nov. 2010.
Takahashi et al., "Three lateral osteotomy designs for bilateral sagittal split osteotomy: biomechanical evaluation with three-dimensional finite element analysis", Head & Face Medicine, vol. 6, No. 4, Mar. 2010, pp. 1-10.

* cited by examiner

TECHNIQUE FOR GENERATING A BONE PLATE DESIGN

CROSS-REFERENCE TO RELATED APPLICATION

The present application is a national phase entry under 35 U.S.C. § 371 of International Application No. PCT/EP2011/006314 filed Dec. 14, 2011, published in English, the disclosure of which is hereby incorporated herein by reference.

TECHNICAL FIELD

The present disclosure generally relates to surgical implants in the form of bone plates. In particular, a technique that enables the computer-implemented design and manufacturing of a bone plate is presented. The technique may be implemented in the form of a method, device or computer-program product.

BACKGROUND

In the past bone plates were available only in a limited variety. For a particular bone type, one or more generic bone plates were offered. Depending on the nature of, for example, a particular fracture, a surgeon had to manually customize the generic bone plate according to fracture-specific needs. Such customizations typically included bending operations to conform the plate to the shape of a bone and cutting operations to adjust a length of the plate.

Today, bone plates are not only offered for specific bone types, but also in various designs for individual types of bone fractures. Moreover, bone plates are also designed based on patient-specific data. In this regard U.S. Pat. No. 6,978,188 B1 discloses a method for contouring a bone reconstruction plate based on medical image data representative of a patient's anatomy. A reconstruction plate is generally employed for covering (e.g., bridging) a bone gap that resulted from removal of a bone portion. The bone gap may be filled with bone material taken from other bones of the patient, wherein the reconstruction plate takes the load of the removed bone portion while the added bone material integrates with the remaining bone.

The bone plate contouring approach of U.S. Pat. No. 6,978,188 B1 includes a three-dimensional surface reconstruction of the removed bone portion based on the medical image data. The three-dimensional surface reconstruction is used to create a representation of a template of the bone plate that is contoured to fit the patient's anatomy. In a last step, the template is manufactured using a rapid prototyping process. The resulting template with its customized contour can be used for implantation or for pre-contouring an implantable plate prior to surgery.

Another computer-implemented technique for designing an implant such as a bone plate is known from US 2009/0149977 A1 (now abandoned). The technique comprises visualizing patient-specific data to permit a surgeon to manipulate a virtual model of the patient's anatomy, the implant, or both, until the implant is ideally positioned within the virtual model. For designing, modifying or manipulating a virtual image of the implant, an interaction with the virtual model of the anatomy takes place. Specifically, the virtual model of the anatomy is altered in a first step. In a second step a standard bone plate is selected from a list of virtual plates and placed in the desired position on the altered virtual model. Then, the selected standard bone plate is automatically adapted to fit an amount of bone displacement and surface contours of the altered virtual model.

It has been found that the plate design approaches suggested in U.S. Pat. No. 6,978,188 B1 and US 2009/0149977 A1 do in many cases still require substantial customization operations by the surgeon in the operating room. It has further been found that this drawback can at least in part be attributed to the fact that the design of the bone plate is to a large extent based on predefined standard bone plates.

SUMMARY

It is an object of the present disclosure to provide a technique for designing a bone plate that overcomes the drawback of the prior art design processes.

According to one aspect, a computer-implemented method of generating a data set that geometrically defines a bone plate design is provided, wherein the method comprises visualizing, based on shape data of a bone, a bone model on a display device, deriving, responsive to a user interaction signal that is indicative of a user interaction relative to the bone model, plate design data representative of a plate-specific design property, and generating a data set that geometrically defines a bone plate design from at least the plate design data and one or more generic plate parameters.

The bone plate design may in one example relate to a definition of a bone plate in accordance with the specific needs of a patient (in which case the shape data may be patient-specific shape data) and/or upon creating a new bone plate type according to generic needs, such as the treatment of a particular fracture type (in which case the shape data may be generic shape data). In other words, the present technique may include, but is not restricted to the definition of patient-specific bone plates.

Deriving the plate design data may comprise determining a relationship between a pointer and the bone model. As an example, a position or a projection of the pointer relative to the bone model may be determined. The pointer may be represented on the display device in a graphical form relative to the bone model.

A user-operable input device (such as a mouse, a keyboard, a trackball, a touchscreen and so on) may be provided that permits a generation of the user interaction signal. A user-operable input device may also permit a positioning of the pointer relative to the bone model on the display device. The user interaction signal may be generated using the same input device that is used to position the pointer, or using another input device.

In one implementation, the relationship between the pointer and the bone model is determined at the point in time when the user interaction signal is generated (e.g., by clicking a mouse button or hitting a keyboard key). The user interaction signal may in such a case be indicative that the user has moved the pointer in a selected relationship with respect to the bone model (on the display device and/or in a coordinate system of the bone model).

Deriving the plate design data may comprise determining one or more points relative to the bone model. As an example, an individual point may be determined from a specific relationship between the pointer and the bone model. As such, the specific point may correspond to a position or projection of the pointer relative to the bone model. For each individual point an individual user interaction signal may occur.

The one or more points may be comprised by the plate design data. Moreover, the one or more points may be determined in a coordinate system associated with at least one of the bone model and the shape data. In one example the plate design data are also provided in that coordinate system or a coordinate system derived therefrom.

The one or more points may be derived to lie on a bone surface (e.g., as defined by the bone model or the shape data). In this regard, the bone model may be realized in the form of a surface model or may at least comprise corresponding surface data.

In one example, the location of a specific point on the bone surface may be derived by projecting a position of the pointer onto the bone surface (e.g., responsive to the user interaction signal).

The one or more points may be visualized relative to the bone model on the display device. Furthermore, a manipulation of the one or more points may be visualized on the display device. The manipulation may comprise at least one of a deletion, insertion and shifting of a point. The plate design data may be adapted in accordance with the manipulation.

In one implementation, the one or more points are representative of a center position of one or more fixation openings or other characteristic features (such as the position or orientation of plate segments) of the bone plate design. In such an implementation, the one or more points may be visualized in the form of a graphical representation of the one or more associated fixation openings or other characteristic features. As an example, a specific point may be visualized in the form of a cross, ring or circle, wherein a center of the cross, ring or circle is indicative of that point.

Based on a sequence of two or more points a curve may be determined. The curve may be a polygonal curve, a spline or a simply a (e.g., straight) line. In one realization, the curve may be manipulated via a user interaction (e.g., in one, two or three dimensions).

The curve may be representative of an (e.g., overall) extension of the bone plate or of one or more plate segments of the bone plate. Moreover the plate design data may comprise curve data indicative of the extension of the bone plate design or of the one or more plate segments.

The method may further comprise visualizing the curve on the display device. Furthermore, the visualized curve may be adapted responsive to the manipulation of the one or more points or of the curve. The corresponding plate design data may be adapted correspondingly.

At least one of the plate design data and the data set geometrically defining the bone plate design may be derived or generated based on the shape data. The shape data may be provided in a scaled form (i.e., associated with a scale). In such an implementation the plate design data may be derived to inherit the scaling of the shape data. The shape data may be scaled using metric or non-metric units.

In connection with deriving the plate design data and/or generating the data set defining the bone plate design, the shape data may be analysed to define at least one of an out-of-plane bending and a torsion of the bone plate design. Analysis of the shape data may be performed at locations defined by the plate design data.

The one or more generic plate parameters and/or the plate design data may define at least one of the following plate properties: a number of fixation openings of the bone plate, a geometric property (e.g., a dimension) of a fixation opening of the bone plate, a number of segments of the bone plate, a geometric property of a segment of the bone plate, at least one of a local and a total thickness of the bone plate, at least one of a local and total width of the bone plate, and at least one of a local and a total length of the bone plate. The method may further comprise providing a software based parameter editing function configured to permit editing of the one or more geometric plate parameters.

The method may further comprise visualizing a plate model based on the plate design data. The plate model may comprise a full representation of the bone plate or a schematic representation thereof (e.g., in the form of a linear or non-linear curve schematically representing an extension of the bone plate).

The bone plate may comprise two fixation openings (or multiple pairs of two fixation openings) and a plate segment (e.g., a bar) interconnecting the two fixation openings (or multiple segments interconnecting the two fixation openings of each pair). The method may permit a definition of a geometric property of a segment relative to the bone model and/or the plate model. The definition of the geometric property of the segment may comprise definition of at least one of a length, a width, a thickness, a course and a curvature of the segment.

On the display device an interconnecting line between the two fixation openings that is representative of the segment may be visualized. Moreover, the method may permit a manipulation of the interconnecting line for defining the geometric property of the segment. The resulting interconnecting line may be a portion of the curve discussed above or the curve as such.

In one implementation the bone comprises at least one bone portion that is missing or to be removed, and the bone plate may be adapted to extend at least partially over a bone gap previously filled by the bone portion that is missing or to be removed. The bone plate may thus be realized in the form of a bone reconstruction plate. The bone reconstruction plate may be configured to bridge the bone gap. A software-based resection tool may be provided that is configured to define, responsive to a user interaction signal indicative of a user interaction relative to the bone model, resection data. The resection data may define one, two or more resection planes indicative of the bone portion that is to be removed.

Moreover, reconstruction data for the bone portion that is missing or to be removed may be generated. Generation of the reconstruction data may comprise a virtual reconstruction, for example by freehand drawing, by bone graft, by mirroring, by a statistical shape model or by any combination thereof. The data set defining the bone plate design may be further generated from the resulting reconstruction data. As an example, a bone plate contour in the region of the bone gap may be determined from the reconstruction data.

The data set defining the bone plate design may be generated such that a first plate portion extending over the bone gap is offset, relative to a second plate portion adjacent to the bone gap, into the bone gap. The first plate portion may thus extend into a space previously filled by the bone portion that is missing or to be removed.

The step of generating the data set defining the bone plate design may comprise a processing of the shape data and, optionally, the reconstruction data. The processing of the shape data and, optionally, the reconstruction data may be performed to define at least one of the following geometric properties of the customized bone plate: a bone plate contour (e.g., on a side facing the bone), a distance between two plate features (such as two fixation openings), one or more in-plate-bendings, a plate torsion, one or more out-of-plate-bendings, one or more local widths (e.g., of a plate segment), a total width, one or more local lengths (e.g., of a plate segment) and a total length.

The shape data may have been obtained by medical imaging (e.g., using Computer Tomography, CT, or in any manner) and may be provided in the form of a data file. The shape data may be patient-specific (so that also the bone plate design will be patient-specific) or generic. Generic shape data may, for example, be obtained by processing (e.g., averaging) a set of patient-specific shape data from multiple patients. The generic shape data may be gender-specific or age-specific. In one example, the shape data are STL or Digital Imaging and Communications in Medicine (DICOM) data.

According to a further aspect, a computer-implemented method of processing geometric data for a bone plate is provided, wherein the method comprises receiving a data set that geometrically defines a design of a non-planar bone plate, and processing the data set to generate processed geometric data that define in two dimensions an unfolded state of the non-planar bone plate.

In a mathematical sense, the unfolded state may be regarded as a development of the non-planar bone plate in two dimensions. It should be noted that the data set processed in connection with generating the processed geometric data that define an unfolded date of the non-planar bone plate may define a generic or a patient-specific bone plate design.

The method may further comprise manufacturing a planar version of the bone plate based on the processed geometric data. Various manufacturing techniques can be used in this regard, including Computer Aided Manufacturing (CAM) and/or Rapid Prototyping (RP). The bone plate may be manufactured from a material like metal (such as titanium) or any polymer (such as PMMA, PEEK and Medpor®).

The method may further comprise bending, based on the data set that geometrically defines the bone plate design, the planar version of the bone plate to obtain at least one of an out-of-plate bending and a torsion. The bending may be performed in a computer-controlled manner using a suitable robot tool. The planar version of the bone plate may comprise at least one in-plane bending.

As stated above, the bone plate may be a bone reconstruction plate. Additionally, or as an alternative, the bone plate may be configured to be fixed to at least one of a cranial, facial and mandibular bone, or to a bone of an extremity. The bone plate may be a mandibular reconstruction plate.

Moreover, any of the methods disclosed herein may be performed workflow-driven. Accordingly, a user may be guided through one or more of the method steps based on a software-implemented workflow.

Further provided is a computer product comprising program code portions for performing the steps of any of the methods and method aspects presented herein when the computer program product is executed on a computing device or a set of interconnected computing devices. The computer program product may be stored in one or more computer-readable recording mediums.

Also provided is a device for bone plate design, the device comprising a display device adapted to visualize, based on shape data of a bone, a bone model, and at least one processor adapted to derive, responsive to a user interaction signal that is indicative of a user interaction relative to a bone model, plate design data representative of a plate specific design property, wherein the at least one processor is further adapted to generate a data set that geometrically defines a bone plate design from at least the plate design data and one or more generic plate parameters.

Also provided is a device for processing geometric data for a bone plate, wherein the device comprises an interface adapted to receive a data set that geometrically defines a design of a non-planar bone plate, and at least one processor adapted to process the data set to generate processed geometric data that define in two dimensions an unfolded state of the non-planar bone plate.

Further provided is manufacturing system comprising the device for processing geometric data and another device adapted to manufacture a planar version of the bone plate based on the data set.

According to a still further aspect of the present disclosure, a data set or a data signal comprising the data set that geometrically defines the bone plate design is provided, wherein the data set has been generated as discussed herein.

Still further, a data set or data signal comprising processed geometric data of a bone plate design is provided, wherein the processed geometric data have been generated as discussed herein.

As a further aspect, a bone plate for fixation to at least one first bone portion is provided, wherein a second bone portion adjacent to the at least one first bone portion is missing or to be removed prior to plate fixation, and wherein the bone plate comprises at least one first plate portion configured to be fixed to the at least one first bone portion, wherein the at least one first plate portion comprises one or more fixation openings, and a second plate portion configured to extend over a bone gap previously filled by the second bone portion, wherein the second plate portion is offset, relative to a section of the first plate portion adjacent to the bone gap, into the bone gap.

In one implementation, the bone plate comprises two first plate portions arranged on opposites sides of the second plate portion. In such an implementation the bone plate may be configured to bridge the bone gap.

BRIEF DESCRIPTION OF THE DRAWINGS

Further aspects, details and advantages of the present disclosure will become apparent from the following description of exemplary embodiments in conjunction with the accompanying drawings, wherein.

DETAILED DESCRIPTION

In the following description of exemplary embodiments, for purposes of explanation and not limitation, specific details are set forth, such as particular methods, functions and procedures, in order to provide a thorough understanding of the technique presented herein. It will be apparent to one skilled in the art that this technique may be practiced in other embodiments that depart from these specific details. For example, while the technique presented herein will in the following primarily be discussed in connection with mandibular reconstruction plates, it will be readily apparent that the technique can likewise applied to bone plates for implantation in other regions of the human or animal body.

Moreover, those skilled in the art will appreciate that the methods, functions and steps explained herein may be implemented using software functioning in conjunction with a programmed microprocessor, an Application Specific Integrated Circuit (ASIC), a Digital Signal Processor (DSP) or a general purpose computer. It will also be appreciated that while the following embodiments will primarily be described in the context of methods and devices, the present disclosure may also be embodied in a computer program product which can be loaded to run on a computer or a distributed computer system comprising one or more processors and one or more memories functioning as storage, wherein the one or more memories are encoded with one or more programs that may perform the methods, functions and steps disclosed herein.

Figure 1:
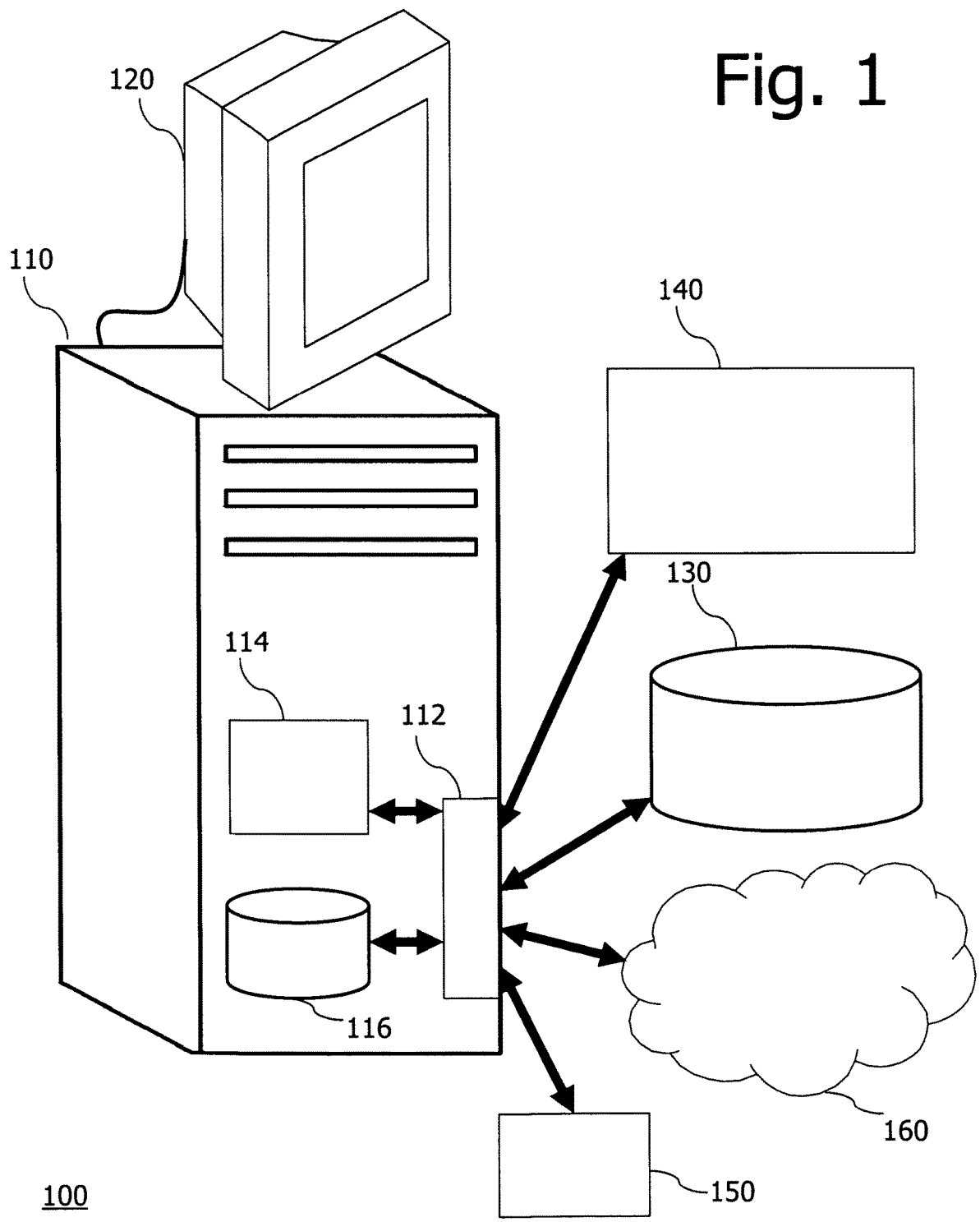
FIG. 1 schematically illustrates an embodiment of a system for designing and manufacturing a bone plate.

FIG. 1 illustrates an embodiment of a system 100 for bone plate design and bone plate manufacturing. As illustrated in FIG. 1, the system 100 comprises a computing device 110 (such a personal computer), a display device 120 (such as a computer monitor), a storage 130 (such as hard disk or a semiconductor memory in which a data base is provided) and a manufacturing device 140 (such as a rapid prototyping device or any programmable machining device). The system 100 further comprises at least one user-operable input device 150 (such as a keyboard, a mouse or a trackball) for generating or triggering the generation of user interaction signals. In one implementation, the display device 120 and the input device 150 may be integrated into a touchscreen.

The computing device 110 comprises an interface 112, at least one processor 114 (such as a Central Processing Unit, CPU) and a storage 116 (such as a hard disk or a semiconductor memory). The interface 112 is configured as an input/output interface for establishing a communication between the computing device 110 on the one hand and, on the other hand, the display device 120, the storage 130, the manufacturing device 140, the input device 150 and a computer network 160 (such as a Local Area Network, LAN, and/or the Internet). The interface 112 can be realized in the form of one or more hardware components, one or more software components or a combination of one or more hardware components and one or more software components.

In the following, exemplary modes of operation of the system 100 illustrated in FIG. 1 will be discussed in more detail with reference to the remaining drawings. It should be noted that the operational procedures discussed herein could also be implemented in a system having a configuration different from that of the system 100 of FIG. 1.

Figure 2:
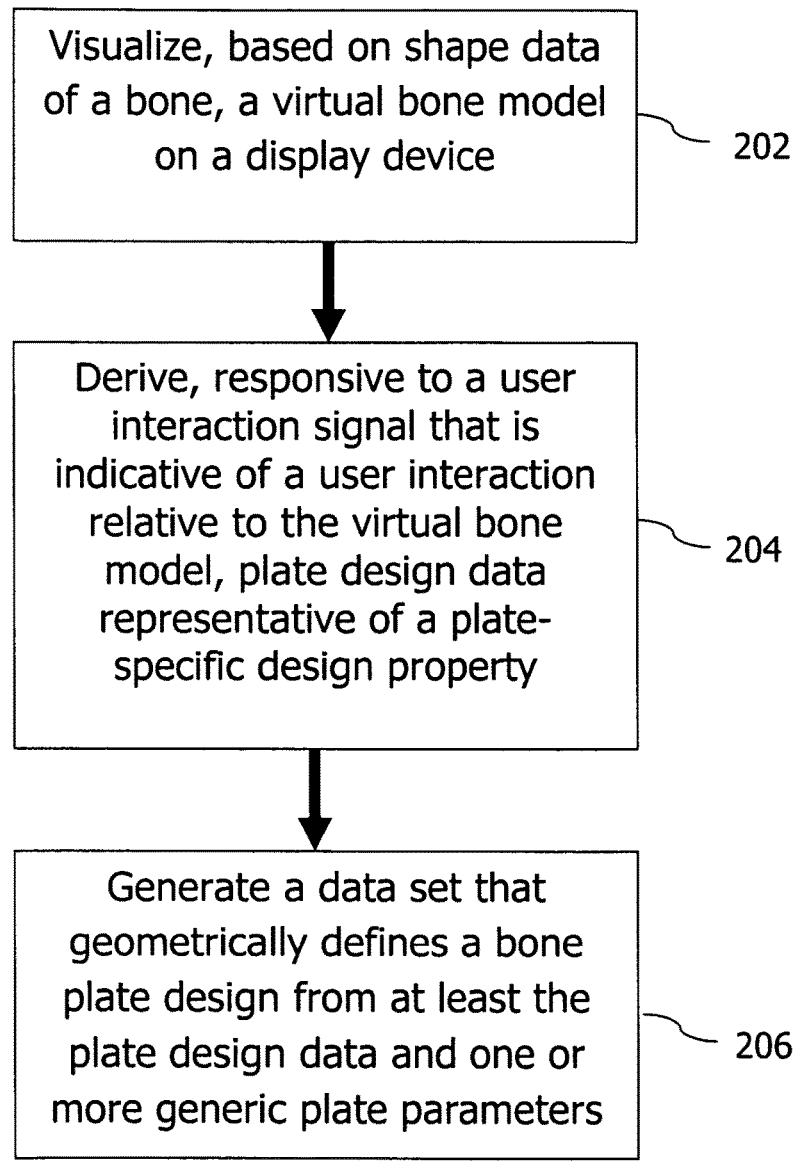
FIG. 2 is a flow diagram illustrating a first embodiment of a method for designing a bone plate.

FIG. 2 shows a flow diagram 200 that illustrates an embodiment of a computer-implemented method of generating a data set that geometrically defines a bone plate design. The generation of a data set illustrated in FIG. 2 will be discussed in more detail with reference to the exemplary hardware components illustrated in FIG. 1.

In an optional step not illustrated in FIG. 2, the computing device 110 obtains shape data of a bone to which a bone plate is to be fixed. The shape data is received from any one of the internal storage 116, the external storage 130 and the computer network 160. In one implementation, the shape data are patient-specific CT data conforming to the DICOM standard. It will be appreciated that in other implementations the shape data could be generated otherwise, could conform to other standards or could be generic shape data.

After the shape data have been obtained, in step 202 the processor 114 processes the shape data. The processing operations carried out by the processor 114 in this regard visualize on the display device 120 a (virtual) three-dimensional model of the bone. It will be appreciated that the processing of the shape data may involve further processing operations, such as converting the CT data to surface data (in accordance with, for example, the STL standard) prior to visualisation thereof.

In a next step 204, a software-based plate design functionality is executed. The plate customization functionality may be stored as program code in the internal storage 116 or the external storage 130. When executed by the processor 114, the plate design functionality derives, responsive to a user interaction signal that is indicative of a user interaction relative to the bone model, plate design data representative of a plate-specific design property.

The user interaction may take place via the input device 150. As an example, the user interaction may involve moving a (virtual) pointer, on the display device 120, relative to the model of the bone to a desired portion and pressing a key of the keyboard, a mouse button or a trackball button. The plate design data may then be derived based on the position of pointer relative to the model of the bone (e.g., in the coordinate system of the bone model and/or the shape data) at the time when the key or button is pressed. As an example, the plate design data thus derived may be indicative of the position of characteristic features of the bone plate to be designed, such as one or more fixation openings, one or more plate segments, and so on. The resulting plate design data may be stored in the internal storage 116, the external storage 130 or both storages 116, 130. Additionally, or as an alternative, the plate design data may be transmitted, via the computer network 160, to a remote computing device (not shown in FIG. 1).

In a further step 206, the processor 114 generates a data set geometrically defining the bone plate design from at least the plate design data and one or more generic plate parameters. The generic plate parameters may be indicative of generic dimensions and/or generic design properties of the bone plate. The processor may process further data in order to generate the plate design data, such as one or more of the shape data, reconstruction data and resection data as will be discussed in more detail below. The resulting plate design data may in one example be indicative of the geometric dimensions and the geometric features of the customized bone plate. As an example, the geometric data may take the form of Computer Aided Design (CAD) data, CAM data, or any other data.

Figure 3:
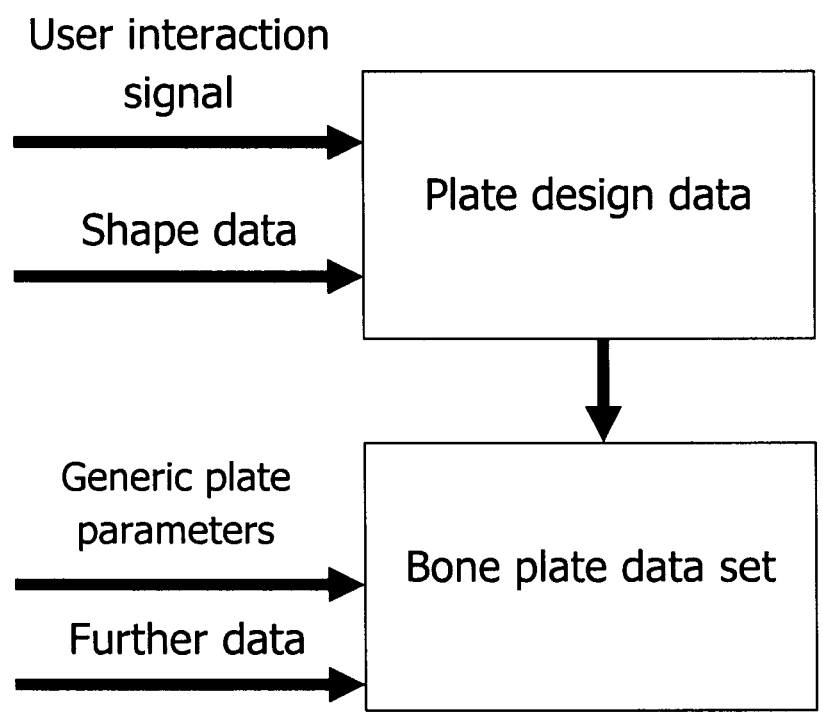
FIG. 3 is a schematic diagram illustrating an exemplary data flow for generating a data set that geometrically defines a bone plate design.

FIG. 3 illustrates in a diagram 280 the basic input and output data according to one embodiment. As illustrated in FIG. 3, the plate design data are derived in one example from the user interaction signal and the shape data, wherein the shape data may be represented (e.g., as surface data) by the bone model. As an example the plate design data may be derived from projecting a virtual position of a pointer on the display device onto a bone surface defined by the bone model. In case the shape data are provided in a scaled form (e.g., in metric units), the plate design data may inherit that scaling of the shape data. In one example, the scaling may be inherited by performing the projection in the (scaled) coordinate system of the shape data and/or the bone model.

Once the plate design data have been derived, the data set that geometrically defines the bone plate design is generated. As illustrated in FIG. 3, the bone plate data that is generated from at least the plate design data and generic plate parameters. Additionally, the shape data (e.g., in the form of surface data) may be taken into account so as to define a bone plate contour. Still further, reconstruction data and/or resection data can be taken into account.

Having described the basic operation of the system 100 with reference to the flow diagram 200 of FIG. 2 and the input/output diagram 280 of FIG. 3, the operation of the system 100 will now be described in more detail with reference to the flow diagram 300 of FIG. 4. The flow diagram 300 of FIG. 4 may be regarded as presenting further details concerning the basic operation that has already been discussed in the context of FIGS. 2 and 3. It should, however, be noted that the operational steps of the flow diagram 300 could in principle also be implemented using a system different from the system 100 illustrated in FIG. 1 and independently of the specific details discussed above with reference to FIGS. 2 and 3.

The technique illustrated in FIG. 4 will be described in the context of designing and manufacturing a mandibular reconstruction plate. It should be noted that in other embodiments bone plates different from such mandibular reconstruction plates may be designed and manufactured. As an example, bone plates for covering cranial openings can be mentioned. The bone plate customization technique of FIG. 4 is performed workflow driven under control of program code residing in the internal storage 116 or the external storage 130.

Figure 4:
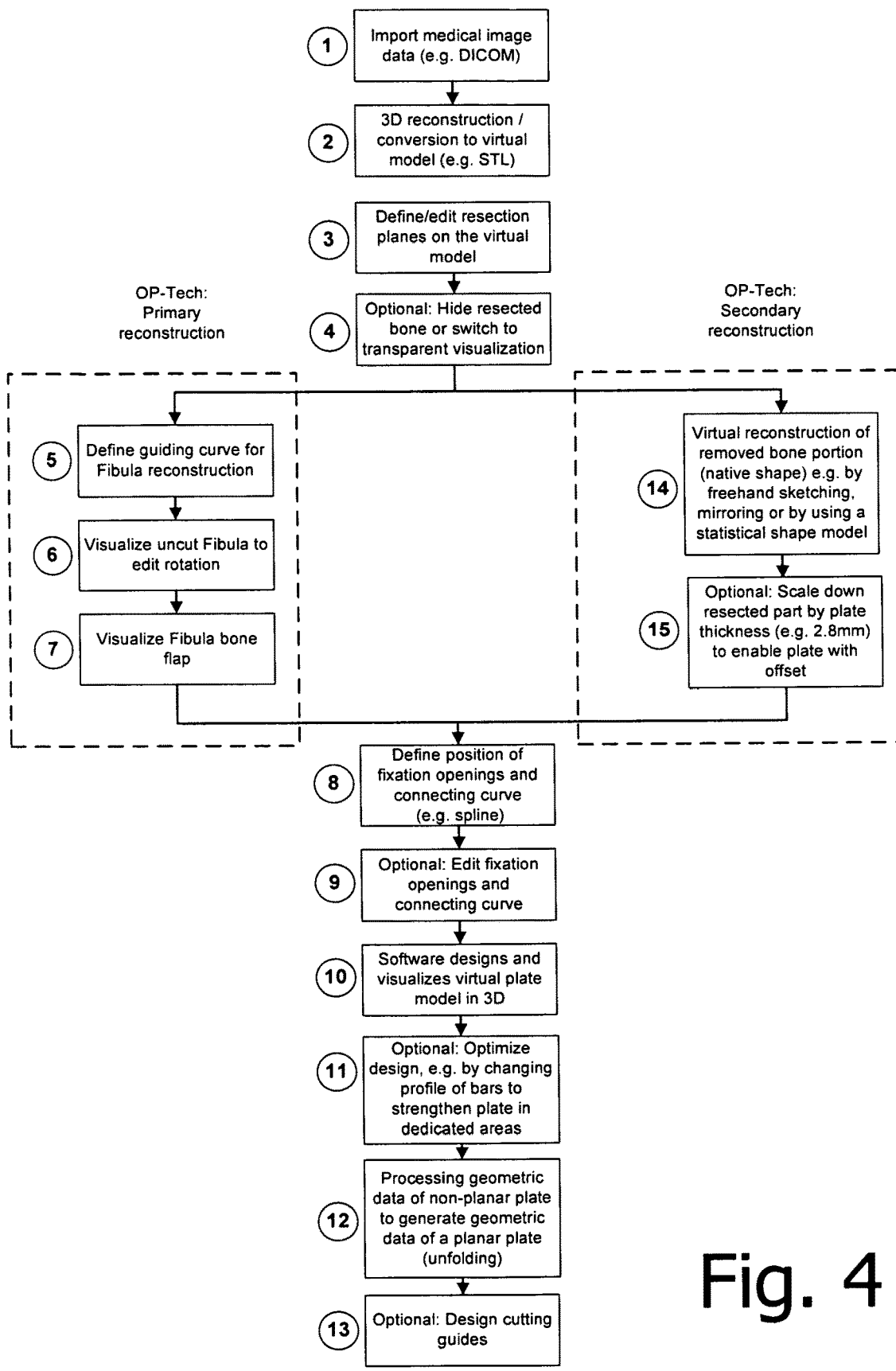
FIG. 4 is a flow diagram illustrating a second embodiment of a method for designing a bone plate.

With reference to the flow diagram 300 of FIG. 4, in a first step the processor 114 imports medical image data such as a DICOM file of the mandible that is to be reconstructed via the interface 112 from the external storage 130 or from a remote site of the computer network 160. In an alternative embodiment, the DICOM file may be read from the internal storage 116. The DICOM file has been prepared by a 3D scanner (using, e.g., CT) and includes a scan of the mandible to be reconstructed.

In a second step of the flow diagram 300 the data (comprising the inherent shape data) included in the imported DICOM file are processed by the processor 114 to generate shape data in the form of bone surface data (e.g., STL data). The resulting bone surface data are representative of a bone model. Based on the bone surface data the processor 114 thus visualizes on the display device 120 a (virtual) model 400 of the bone 410 as illustrated in the upper half of FIG. 5. The second step of the flow diagram 300 of FIG. 4 may thus be regarded to correspond to step 202 of the flow diagram 200 of FIG. 2. As shown in the upper half of FIG. 5, the bone 410 comprises a degenerated bone portion 420 that is to be removed and to be bridged by a mandibular reconstruction plate.

The program code running on the processor 114 comprises a software-based resection functionality that is configured to define, responsive to a user interaction signal indicative of a user interaction relative to the model 400 of the bone 410, resection data. For a definition of the resection data, a (virtual) pointer 430 can be moved relative to the model 400 under control of the input device 150. By repeatedly confirming desired positions of the pointer 430 relative to the model 400 of the bone 410 (e.g., by pressing a key or a button), resection data in the form of two resection planes 440, 450 in the coordinate system of the model 400 is input by the user (see third step of the flow diagram 300 of FIG. 4). The two resection planes 440, 450 define the bone portion 420 that is to be removed. As shown in the upper half of FIG. 5, the two resection planes 440, 450 are visualized relative to the model 400 of the bone 410.

Figure 5:
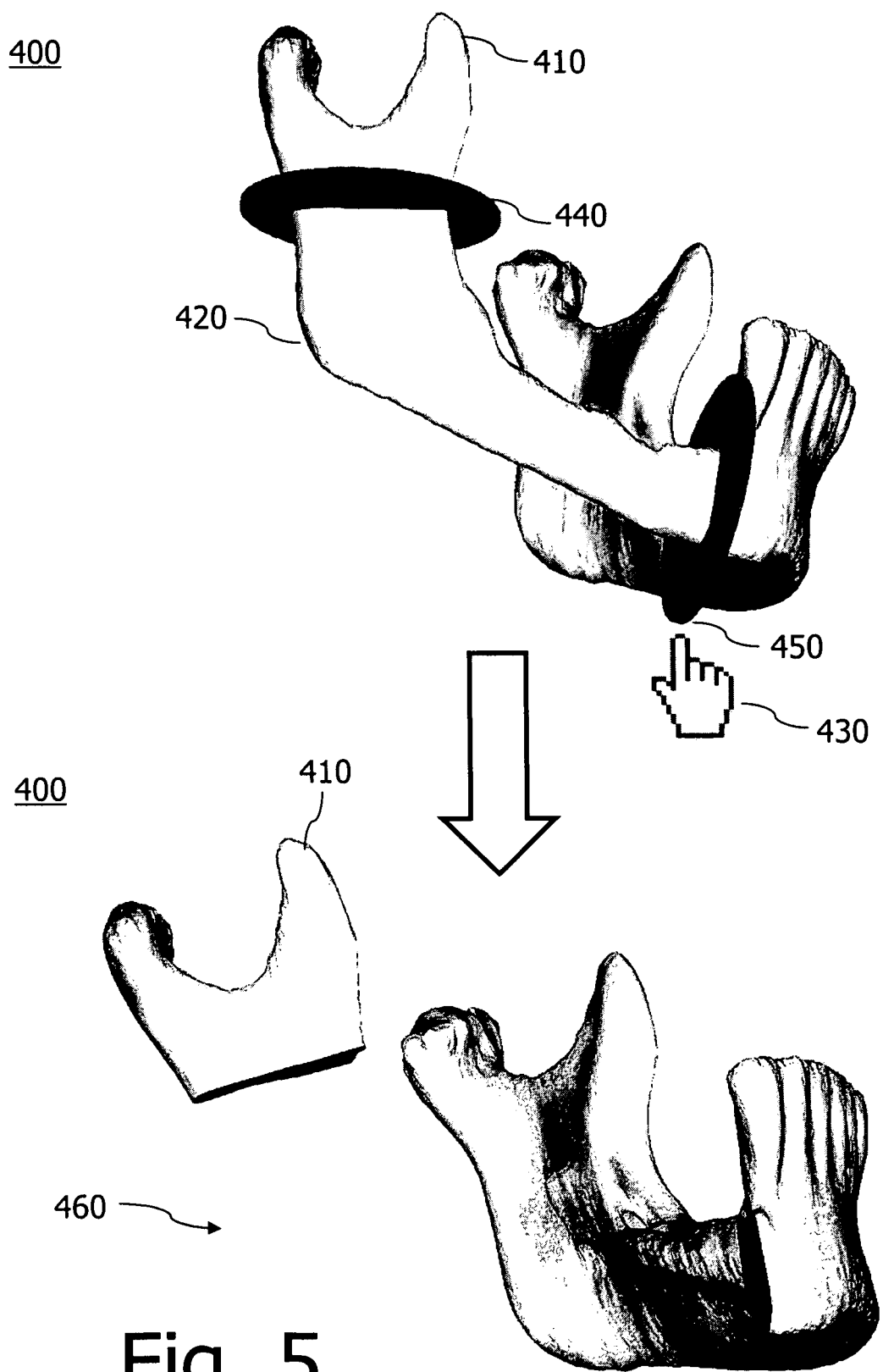
FIG. 5 is a schematic diagram illustrating operation of an embodiment of a software-based resection tool.

In a fourth step of the flow diagram 300 of FIG. 4, the resected bone portion 420 is hidden as illustrated in the lower half of FIG. 5. Alternatively, the resected bone portion 420 may be transparently visualized or marked otherwise (e.g., using a specific colour). The model 400 of the bone 410 illustrated in the lower half of FIG. 5 thus shows a bone gap 460 that was previously filled by the bone portion 420 that is to be removed.

The further course of the workflow illustrated in FIG. 4 depends on the surgical technique selected for reconstructing the mandible. In this regard primary and secondary construction approaches can be distinguished. According to the primary reconstruction approach, the removed bone portion 420 is replaced by bone material taken, for example, from the fibula or rib. According to the secondary reconstruction approach, the removed bone portion 420 is simply bridged by the mandibular reconstruction plate. A replacement of the removed bone portion 420 will then take place in a separate (later) surgical procedure.

Figure 6:
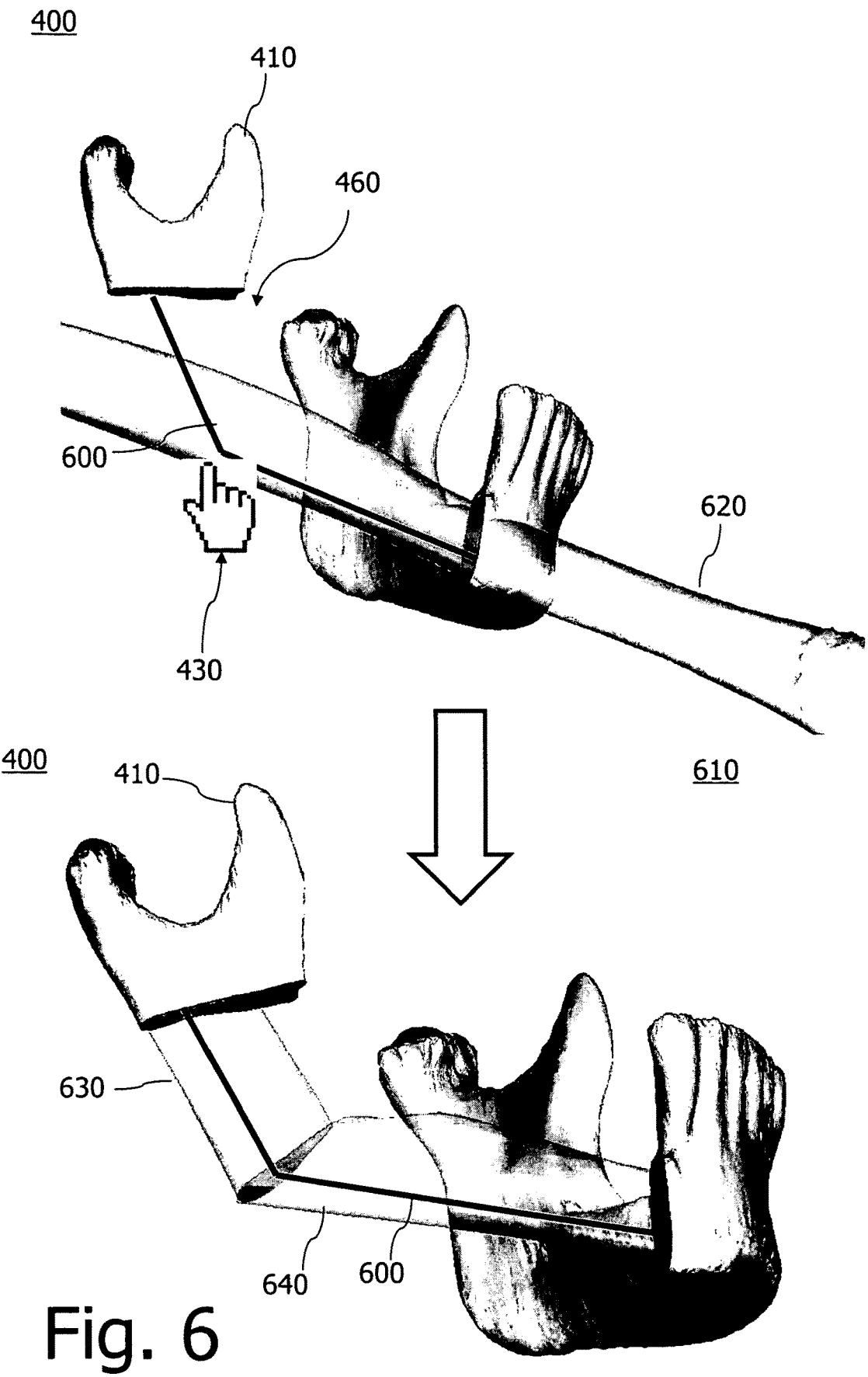
FIG. 6 is a schematic diagram illustrating operation of an embodiment of generating reconstruction data using bone graft.

In the following the workflow illustrated in FIG. 4 will first be described with respect to the primary reconstruction approach based on bone material taken from the fibula. With reference to FIG. 6, in a fifth step of the flow diagram of FIG. 4 a guiding curve 600 for fibula-base reconstruction is defined responsive to user interaction signals indicative of user interactions relative to the model 400 of the bone 410. Specifically, the guiding curve 600 is defined by moving the pointer 430 under the control by the input device 150 to selected (virtual) positions relative to the model 400 and then pressing a key or button to confirm a start point, intermediate point and end point of the guiding curve 600. To this end, a position of the pointer 430 may be projected onto the (hidden) bone surface of the model 400, wherein the resulting projections constitute those points in the coordinate system of the bone model 400.

In a sixth step of the flow diagram 300 of FIG. 3, which is also illustrated in the upper half of FIG. 6, a (virtual) model 610 of the uncut fibula 620 is displayed on the display device 120. The model 610 of the uncut fibula 620 is generated from shape data in a similar manner as the virtual model 400 of the bone 410. The model 610 of the fibula 620 may be moved and/or rotated relative to the model 400 of the bone 410 via a user interaction (employing the pointer 430 and the associated input device 150). The user is also given opportunity to virtually cut the fibula 620, wherein the resulting fibula portions 630, 640 are automatically aligned along the guiding curve 600 and visualized on behalf of the removed bone portion 620 as illustrated in the lower half of FIG. 6 (in accordance with the seventh step of the flow diagram in FIG. 4).

Figure 7:
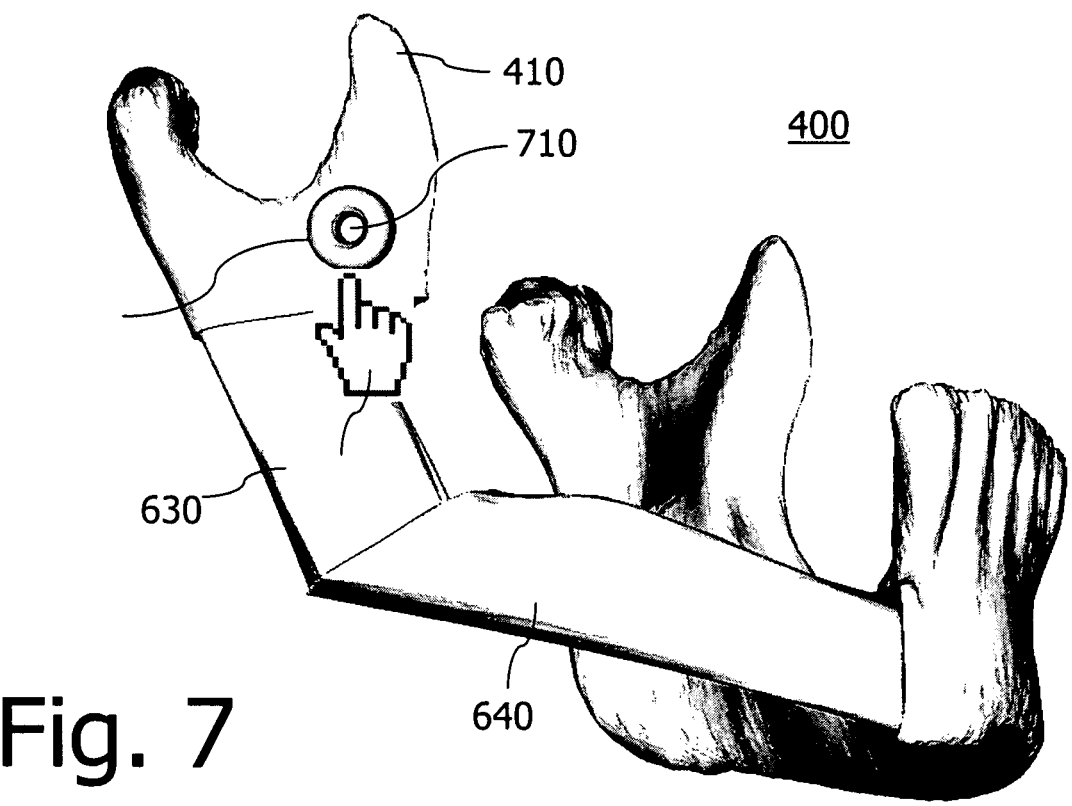
FIGS. 7 to 11 are a schematic diagrams illustrating operation of an embodiment of defining a plate-specific design property represented by positions of fixation openings.

In an eighth step of the flow diagram 300 of FIG. 4, a software-based plate design functionality is invoked by the processor 114 for defining a bone plate design as illustrated in FIG. 7.

As is known in the art, mandibular reconstruction plates comprise a plurality of fixation openings. Bone fixation members (such as bone screws, bone pegs or K-wires) are inserted into the fixation openings for fixing the bone plate to bone. In the embodiment illustrated in FIG. 7, the plate design functionality is configured to permit the definition of positions for a plurality of fixation openings 710 relative to the model 400 of the bone 410. To this end, the pointer 430 is moved to a desired (virtual) position of a fixation opening 710 relative to the model 400 of the bone 410 in a first step. Once the desired position has been reached, a key or button of the input device 150 is pressed. Pressing of the key or button with the pointer 430 being positioned at the desired position of the fixation opening 710 is an input operation. Specifically, upon pressing the key or button a user interaction signal is generated.

Responsive to the user interaction signal the current position of the pointer 430 relative to the bone model 400 is determined. Based on the position of the pointer 430 relative to the bone model 400, a point in the coordinate system of the bone model is determined. The point may be determined by projecting the position of the pointer 430 onto a bone surface defined by the bone model 400. The point thus determined is representative of the center of the fixation opening 710 and is confirmed on the display device 120 by superimposing a (virtual) model of a plate ring 720 comprising the fixation opening 710 on the bone model 400 at the selected position. The center of the plate ring 720 indicates the selected position. The corresponding plate design data resulting from that definition may be stored in the local storage 116 in the form of coordinates (e.g., in the coordinate system of the model 400 of the bone 410).

Figure 8:
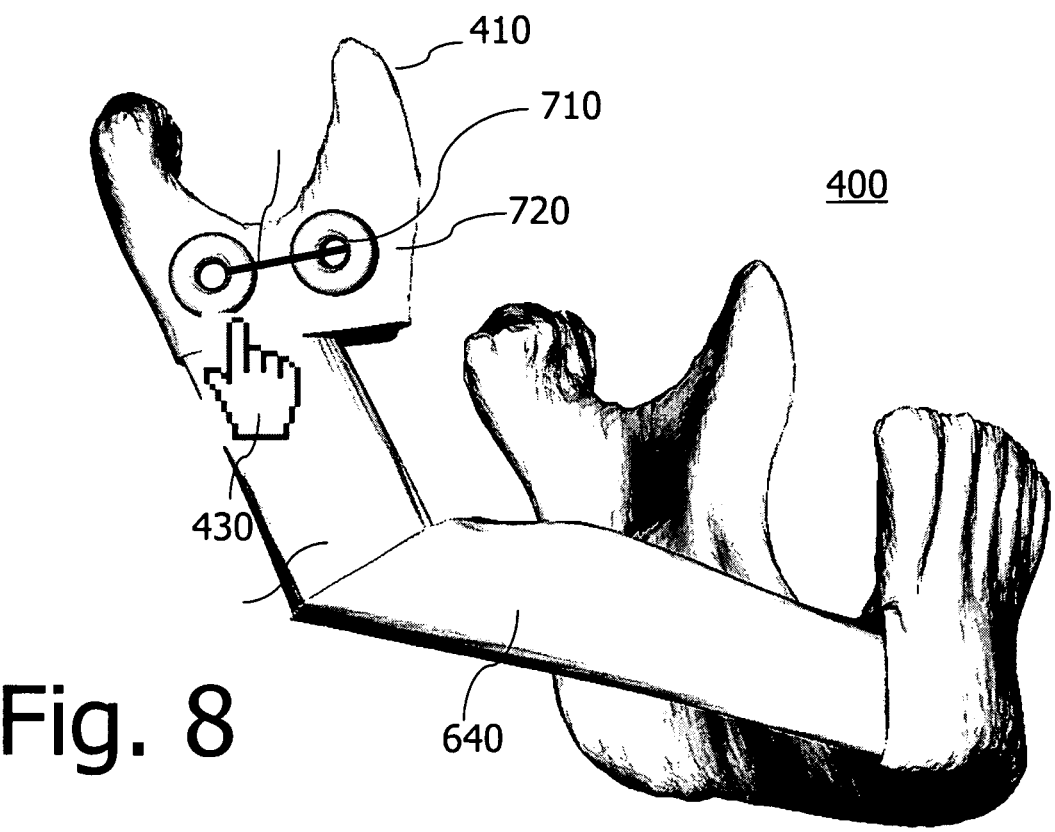
Figure 9:
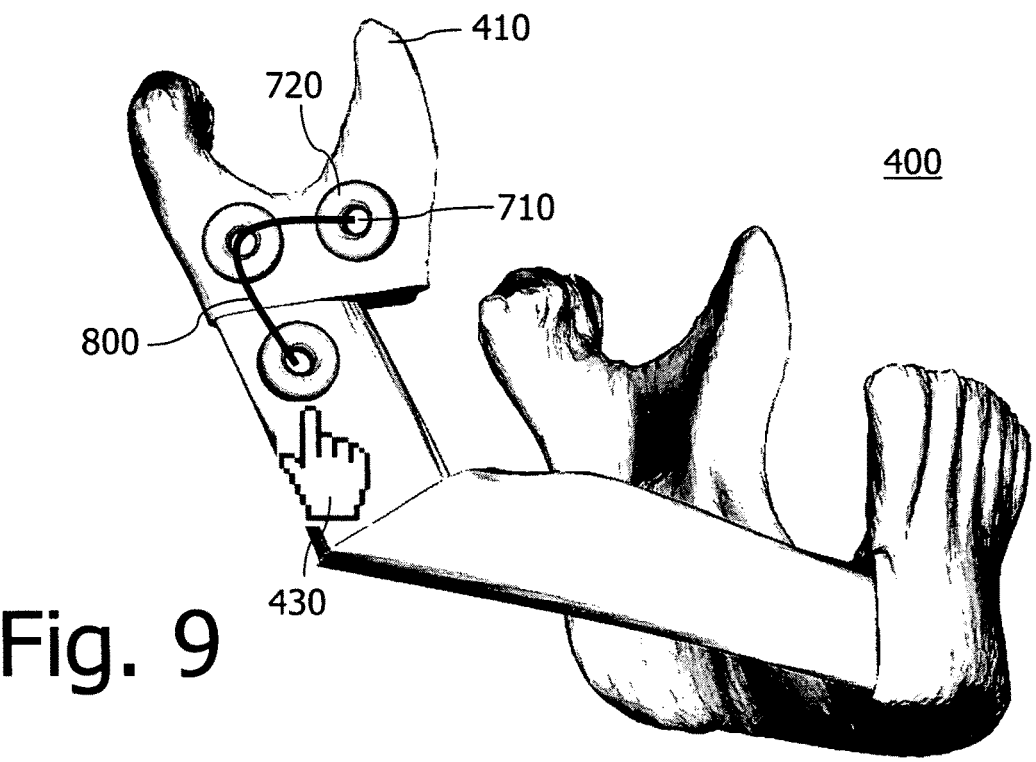
Figure 10:
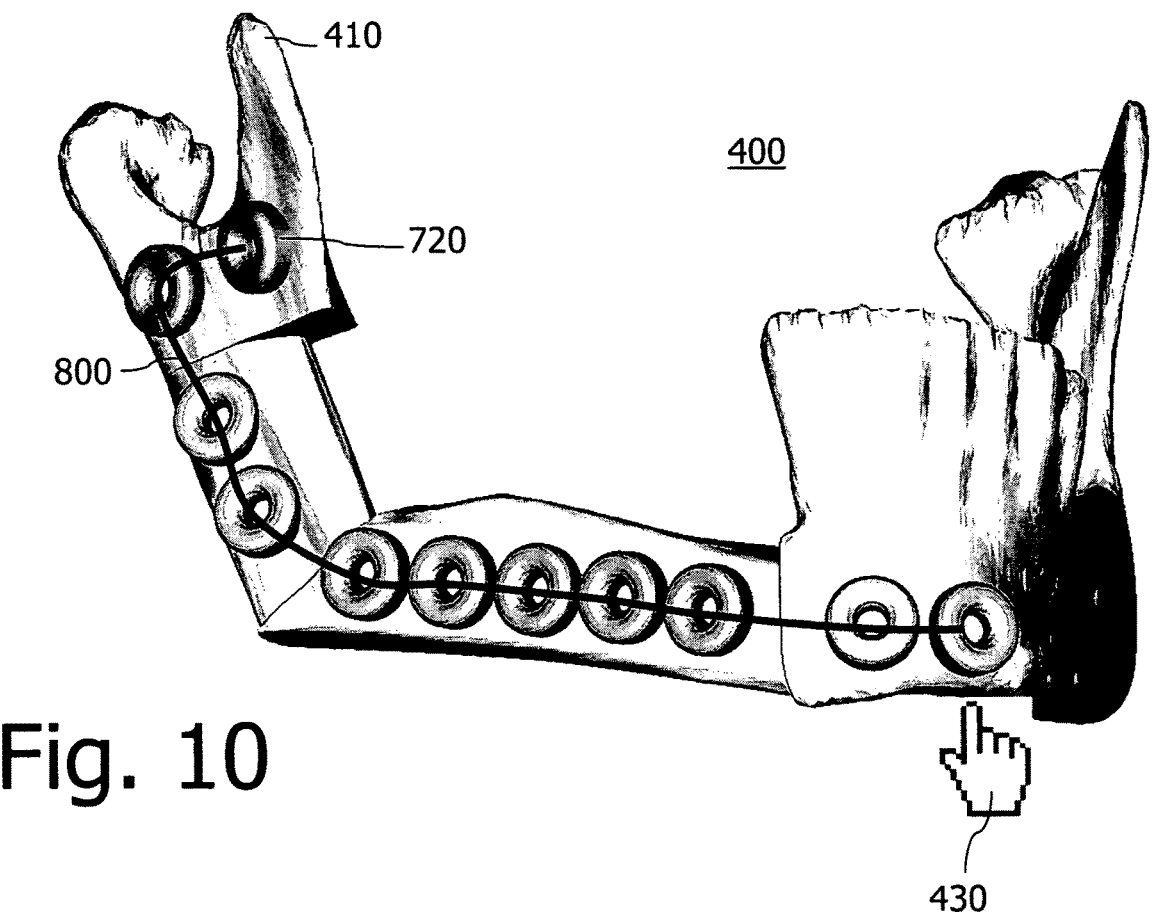

As illustrated in FIGS. 8 to 10, the input operation described above with reference to FIG. 7 may be repeated multiple times to define multiple points relative to the bone model 410. Again, the position of each point defines the center of a fixation opening 710 and is visualized by an associated plate ring 720 on the display device 120.

With reference to FIG. 8, a curve 800 in the form of a spline is visualized as soon as two points (i.e., the positions of two fixation openings 710) have been defined relative to the bone model 400. The curve 800 is newly calculated and extended as additional fixation openings 710 are defined (see FIGS. 9 and 10). The curve 800 (and its underlying point sequence) describes the general extension of the bone plate design and may be stored in the form of plate design data (e.g., as coordinates) in the local storage 416.

The plate design functionality may be configured to permit a manipulation of the one or more fixation openings 710. As indicated by the arrow 810 in FIG. 11, the fixation openings 710 may be manipulated under control of the input device 150 via the pointer 430. The manipulation may comprise a deletion, insertion or shifting of fixation openings 710 (and the underlying points comprised by the plate design data). The plate design data may be adapted in accordance with the manipulation. As an example, if one of the visualized fixation openings 710 is removed, the corresponding point in the plate design data is removed as well. In one optional implementation, also the extension of the curve 800 may be manipulated using the pointer 430.

A section of the curve 800 between two adjacent fixation openings 710 is representative of a plate bar interconnecting the two associated plate rings 720. By manipulating the position of one of the plate rings 720, the interconnecting line starting or ending at the corresponding fixation opening 710 (and thus the associated plate bar) is manipulated as well.

Figure 12:
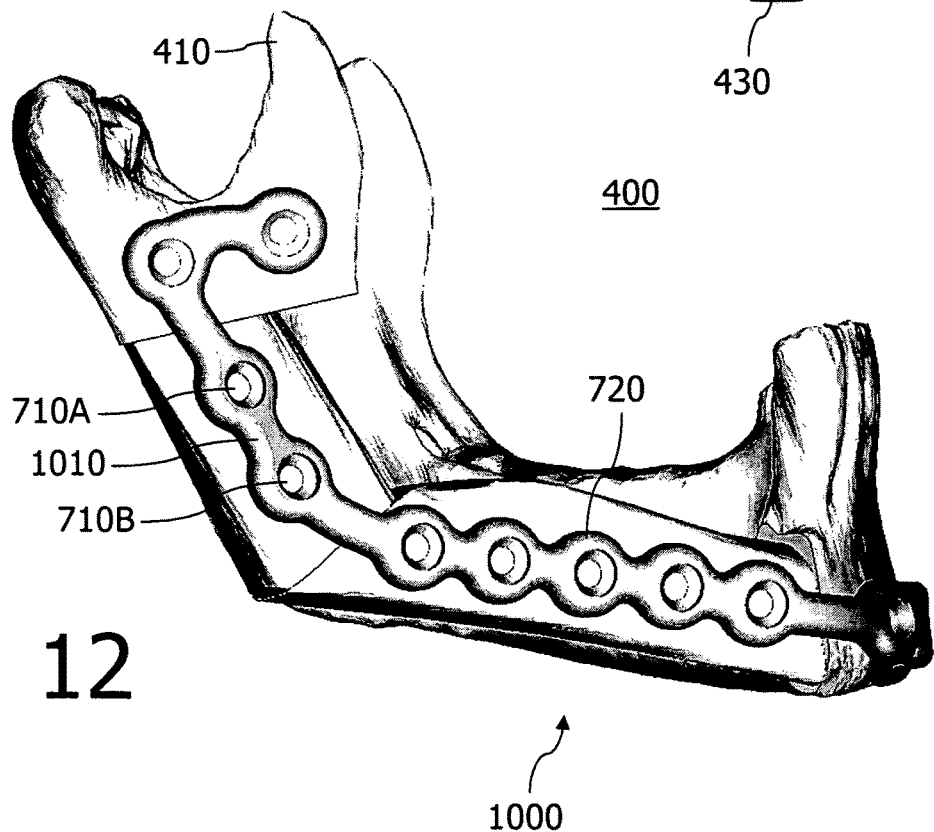
FIG. 12 is a schematic diagram illustrating a model of a bone plate.

Once the locations of all fixation openings 710 have been defined (and, if necessary manipulated), a set of plate design data that defines certain design properties (i.e., the relative locations of the fixation openings 710 and, optionally, a curve 800 defining the bone plate extension) has become available in accordance with step 204 of the flow diagram 200 of FIG. 2. Based on those plate design data a (virtual) model of the bone plate 1000 can be visualized superimposed on the model 400 of the bone 410 as illustrated in FIG. 12. The visualization of the bone plate model in FIG. 12 corresponds to the tenth step of the flow diagram 300 of FIG. 4.

The plate model of FIG. 12 is generated from a combination of generic plate parameters and the plate design data. The generic plate parameters describe generic properties of the bone plate 1000, such as the diameter of the fixation opening 710, the width and the thickness of the plate ring 720 surrounding the fixation opening 710, and the width and the thickness of a plate bar 1010 interconnecting two adjacent fixation openings 710A, 710B.

Figure 13:
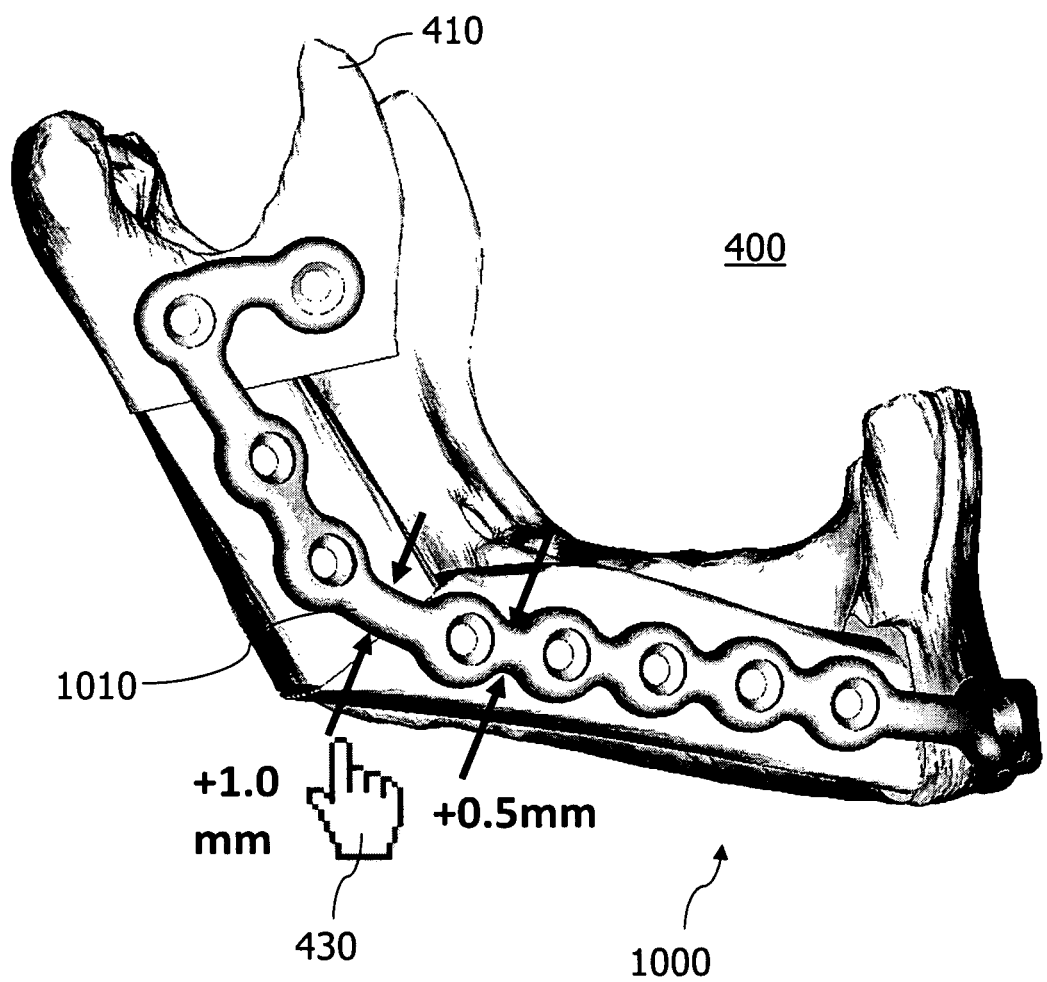
FIG. 13 is a schematic diagram illustrating operation of a further embodiment of defining a plate specific design property represented by plate bars interconnecting two fixation openings each.

In an optional eleventh step of the flow diagram 300 of FIG. 4, the plate design functionality permits a definition or manipulation of one or more design properties of the plate bars 1010. In the example illustrated in FIG. 13, the width of an individual plate bar 1010 may be increased or decreased (e.g., step-wise) via the pointer 430 under control of the input device 150. In this manner, the bone plate 1000 can be strengthened in dedicated areas as desired.

Once the input of the plate design data via the plate design functionality is finished, the workflow illustrated in FIG. 4 proceeds to step 12 of the flow diagram 300. In step 12, a data set is generated by the processor 114 that defines the bone plate design (in accordance with step 206 of flow diagram 200 of FIG. 2). The processor 114 generates the data set from the plate design data input by the user, the shape data included in the STL file, reconstruction data derived for the bone gap 460 and the generic plate parameters (see also FIG. 3). The geometric dimensions of the fixation openings 710 and the plate rings 720 (e.g., their diameter or form) and the plate bars 1010 may be directly derived from the generic plate parameters. Moreover, the contour of the bone plate 1000 (e.g., with respect to in-plane bendings, torsions and/or out-of-plane bendings) to conform to the (reconstructed) bone may be derived from the shape data and, in a region of bone gap 460, from the reconstruction data.

The resulting data set that geometrically define the geometric dimensions of the bone plate design can be stored in a dedicated data base or a data file. The data set may also be sent as a data signal via the computer network 160.

As an example, the data set with the resulting geometric data of bone plate design may directly be transmitted to the manufacturing device 140 so that the actual bone plate 1000 can readily be manufactured. The bone plate 1000 may be manufactured from metal (such as titanium). A metallic material is particularly suited for reconstruction plates that typically have to take a high load. It will be appreciated that other bone plate embodiments, for example for covering cranial openings, may be manufactured from one or more polymers (such as PMMA and PEEK).

In an optional further step of the flow diagram 300 of FIG. 4, one or more cutting guides (or jigs) may be manufactured based on the resection data input in the second step of the flow diagram 300 of FIG. 4. The resection guides may be configured to guide a resection tool (such as a bone saw) in connection with removing the bone portion 420 (see FIG. 5).

Figure 11:
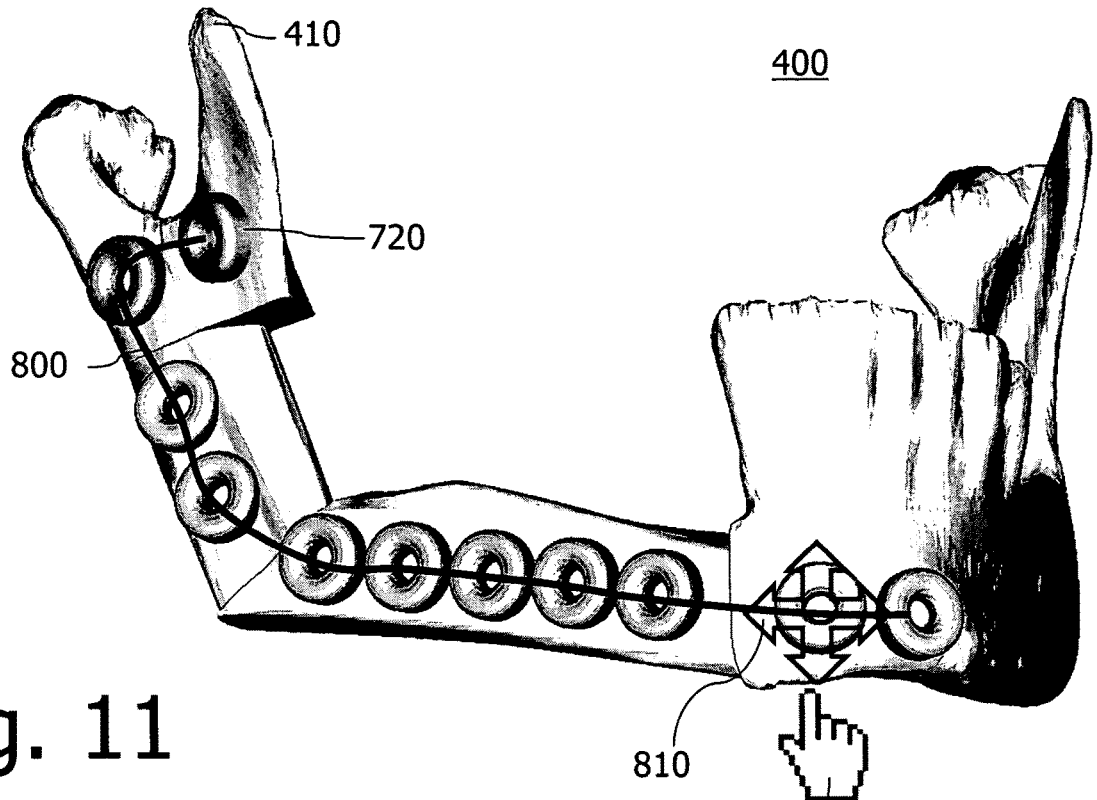
Figure 14:
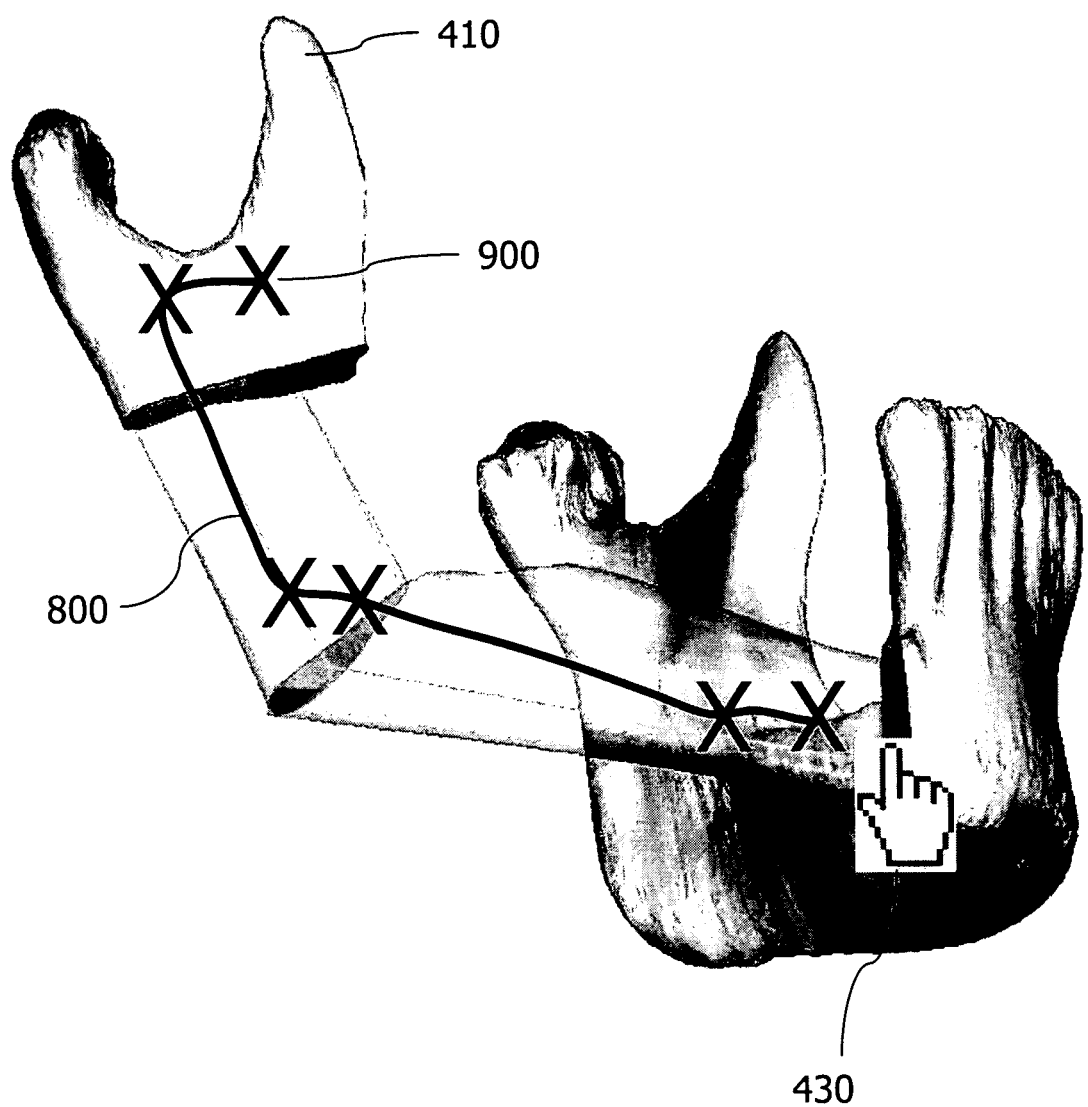
FIG. 14 is a schematic diagram illustrating operation of a further embodiment of defining a plate-specific design property represented by a point sequence that defines a bone plate extension.

FIG. 14 illustrates an alternative approach for defining the course of the mandibular reconstruction plate and the positions of the associated fixation openings 710. In the embodiment discussed with reference to FIGS. 7 to 11, the fixation openings 710 are virtually placed in a first step and the curve 800 is generated in a second step based on the positions of the fixation openings 710. In the embodiment illustrated in FIG. 14, the curve 800 is defined in a first step by inputting a sequence of points 900 relative to the model 400 of the bone 410. Once a sequence of such points 900, that define an extension of the bone plate, has been input, the resulting point sequence is interconnected by the curve 800 (e.g., a spline) as illustrated in FIG. 9. After the extension of the bone plate has been defined, individual fixation openings 710 may then be replaced on that curve 800 (resulting in a similar screen of the display device 120 as shown in FIG. 11).

In the following several additional or alternative aspects of the technique disclosed herein will be discussed. While those aspects will be discussed with particular reference to the preceding embodiments, it will be appreciated that those aspects could also be implemented independently therefrom.

With respect to step 12 of the flow diagram 300 of FIG. 4, the manufacturing of the customized bone plate 1000 as well as an exemplary processing operation preceding the manufacturing will now be described in more detail with reference to the flow diagram 1500 of FIG. 15 and the schematic diagram of FIG. 16.

Figure 15:
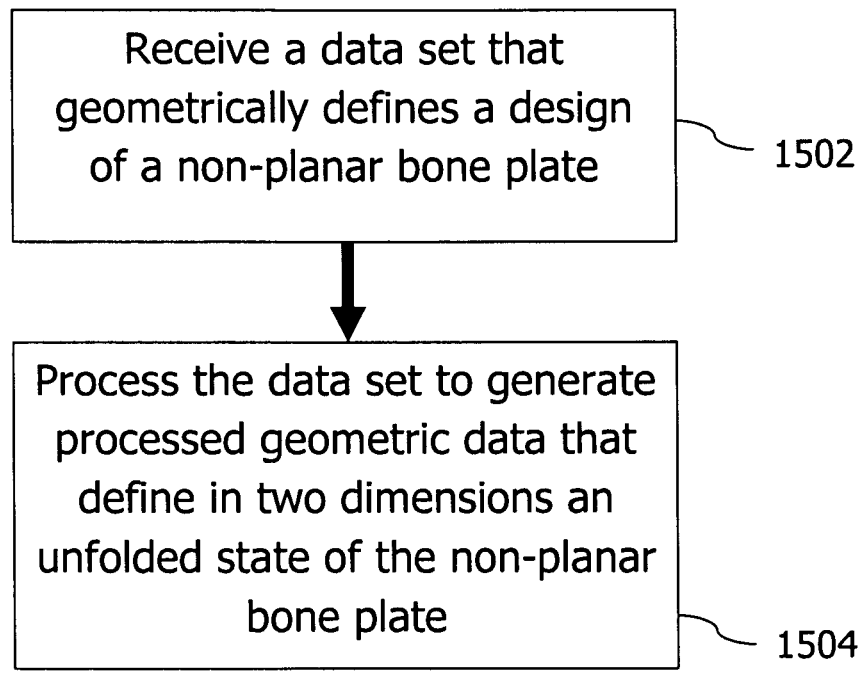
FIG. 15 is a flow diagram illustrating an embodiment of a method for processing geometric data.

The flow diagram 1500 of FIG. 15 illustrates an embodiment of a computer-implemented method of processing geometric data for a bone plate by the processor 114 of the computing device 110 (see FIG. 1) prior to transmitting the processed geometric data to the manufacturing device 140.

In a first step 1502, the processor 114 obtains a data set that geometrically defines of the bone plate design. As an example, the geometric data may be retrieved via the interface 114 from the internal storage 116 (where they may have been stored in step 12 of the flow diagram 300 of FIG. 4). The data set defines a design of the non-planar bone plate 1000 in three dimensions as exemplarily illustrated in the upper half of FIG. 16 in a side view (left) and a top view (right). As mentioned above, the data set specifies the geometric dimensions of the bone plate 1000.

In a subsequent step 1504 the processor 114 processes the data set to generate processed geometric data. The processed geometric data define an unfolded state of the non-planar bone plate 1000 in two dimensions as illustrated in the lower half of FIG. 16.

The processing of the data set in step 1504 involves the application of a mathematical algorithm to the three-dimensional geometric data of the bone plate 1000. The mathematical algorithm transposes the three-dimensional geometric data into processed geometric data describing a mathematical development (i.e., an unfolded state) of the non-planar bone plate 1000 in two-dimensions. This means that the processed geometric data describe only in-plane bendings of the bone plate 1000 as illustrated on the left hand side in the lower half of FIG. 16. The out-of plane bendings of the actual bone plate 1000 (as illustrated in the upper half of FIG. 15) are obtained in a further bending step. The further bending step can be performed by a program-controlled robot tool (e.g., on the basis of the data set geometrically defining the three-dimensional design of the bone plate 1000) or manually.

The processed geometric data generated in step 1504 may take the form of a CAD data set with dimensional information. Alternatively, the processed geometric data may take the form of a CAM data set that may be directly processed by the manufacturing device 140. The manufacturing device 140 thus manufactures a planar, unfolded version of the bone plate 1000 (see lower half of FIG. 16) for being bent (or folded) into the desired three-dimensional form in a later processing step. Since after the manufacturing process no in-plane-bending operations are required, no or less internal stress at critical points of the bone plate 1000 is created.

It should be noted that step 1504 could in principle be omitted in case the manufacturing device 140 is capable of manufacturing the non-planar bone plate 1000. In such a case the data set that defines the shape of the non-planar bone plate 1000, as obtained in step 1502, may be directly passed to the manufacturing device 140.

Having discussed details of step 12 of the flow diagram 300 of FIG. 4 with reference to FIGS. 15 and 16, the secondary reconstruction approach according to steps 14 and 15 of the flow diagram 300 of FIG. 4 will be described next.

As for step 14, the reconstruction data in a case of completely missing bone may be generated by a freehand reconstruction. To this end, a software-based reconstruction functionality may be provided as will now be discussed with reference to FIGS. 17 and 18. The reconstruction functionality may permit input, via freehand drawing relative to the model 400 of the bone 410, of reconstruction data indicative of a missing bone portion (see FIG. 17). Alternatively, or in addition, the missing bone portion could be reconstructed using a statistical shape model. The statistical shape model may have been generated based on generic shape data. Also mirroring techniques as illustrated in FIG. 18 may be used to define the reconstruction data.

Figure 17:
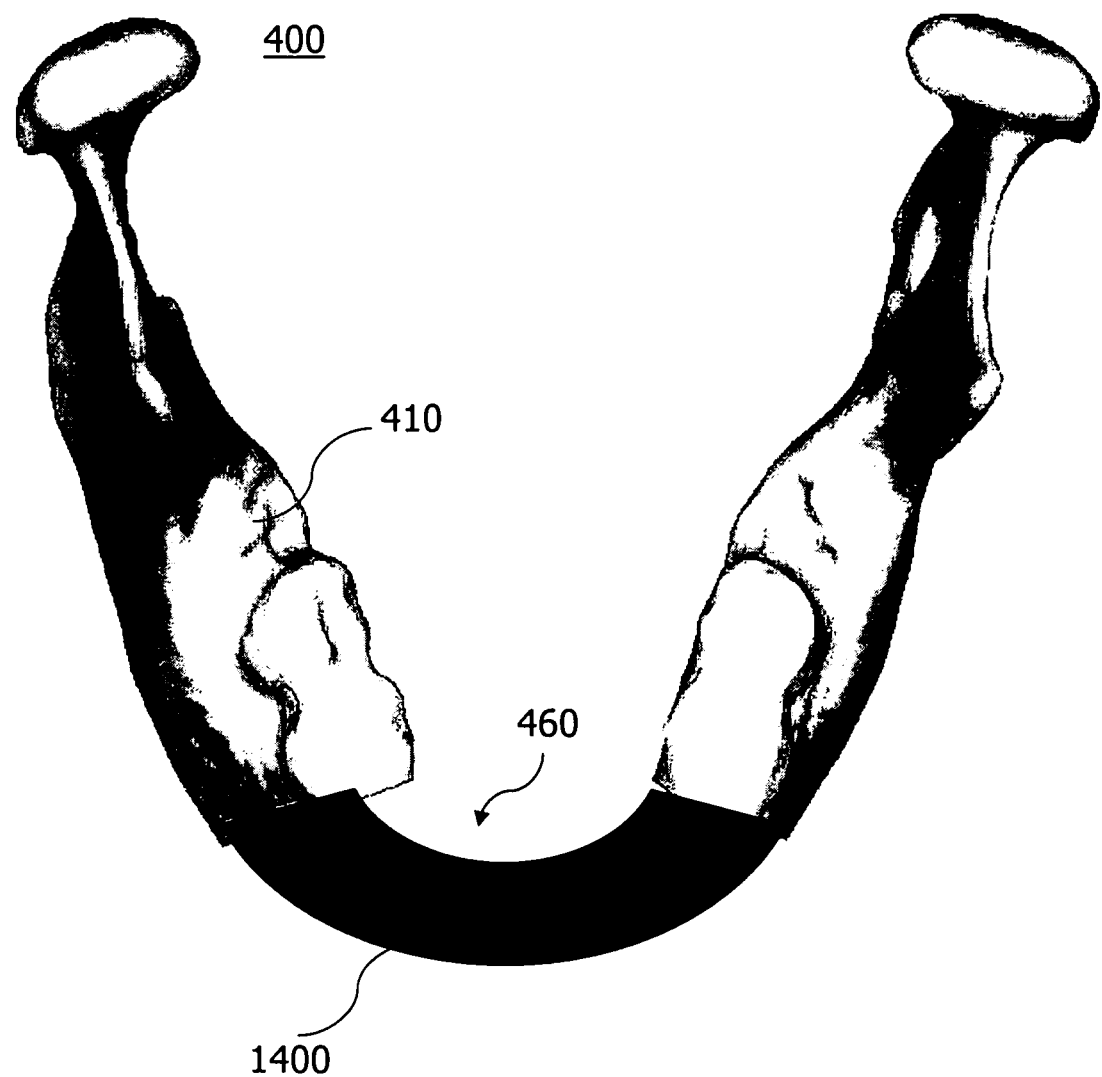
FIG. 17 is a schematic diagram illustrating operation of an embodiment of generating reconstruction data using freehand drawing or a statistical shape model.
Figure 18:
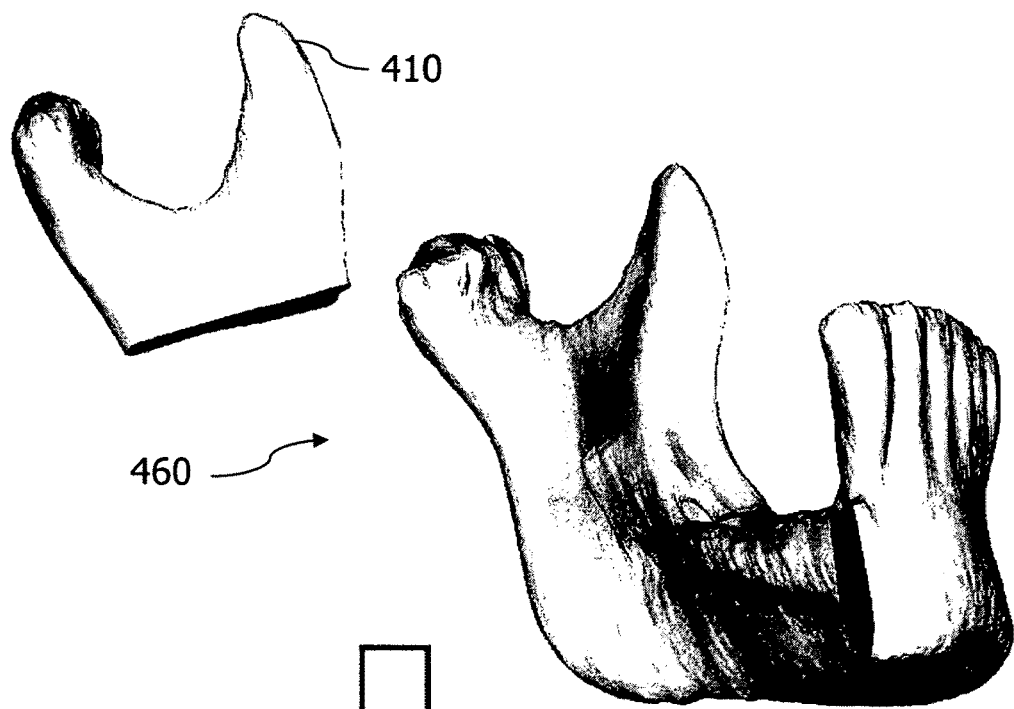
FIG. 18 is a schematic diagram illustrating operation of an embodiment of generating reconstruction data using mirroring techniques.
Figure 18:
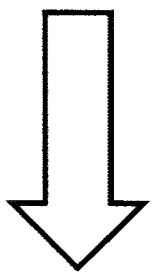
Figure 18:
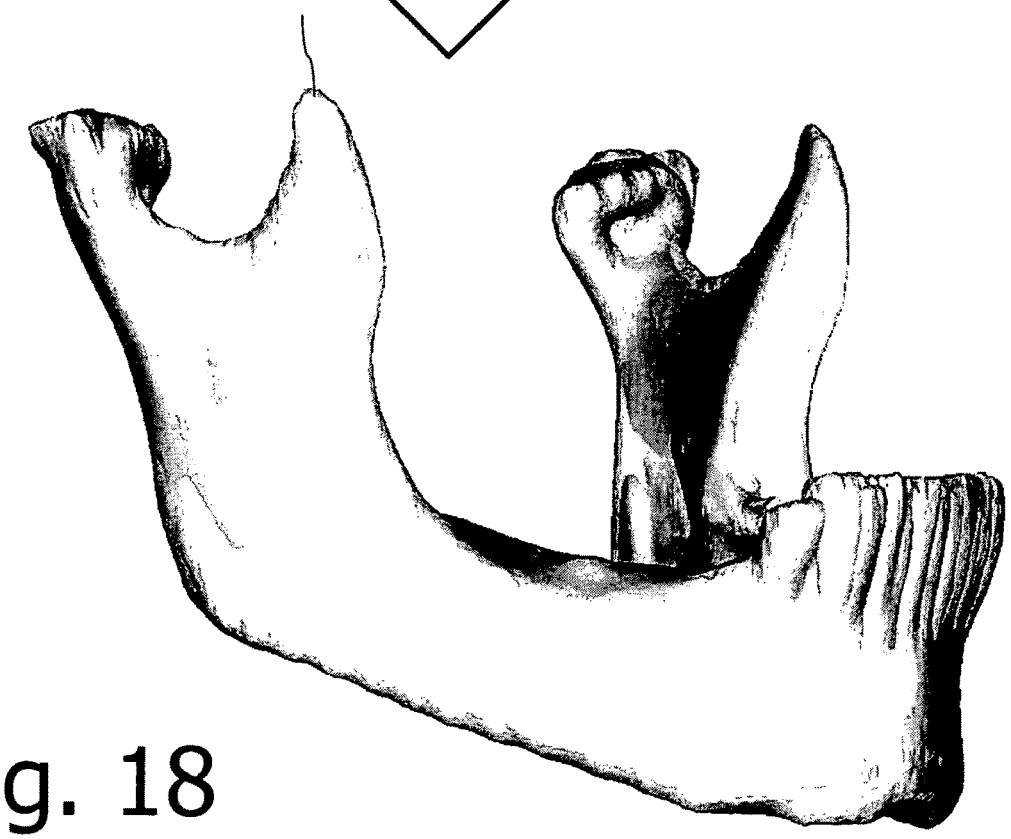

In a next step a virtual reconstruction 1400 of the missing bone portion 420 may be generated based on the reconstruction data and visualized on the display device 120 as shown in FIGS. 17 and 18. Of course, in the context of step 14 of the flow diagram 300 of FIG. 4, the various reconstruction approaches (such as mirroring, free hand reconstruction, reconstruction using bone grafts, and so on) can be combined as needed to derive a virtually reconstructed bone model 400 for visualization purposes.

Figure 16:
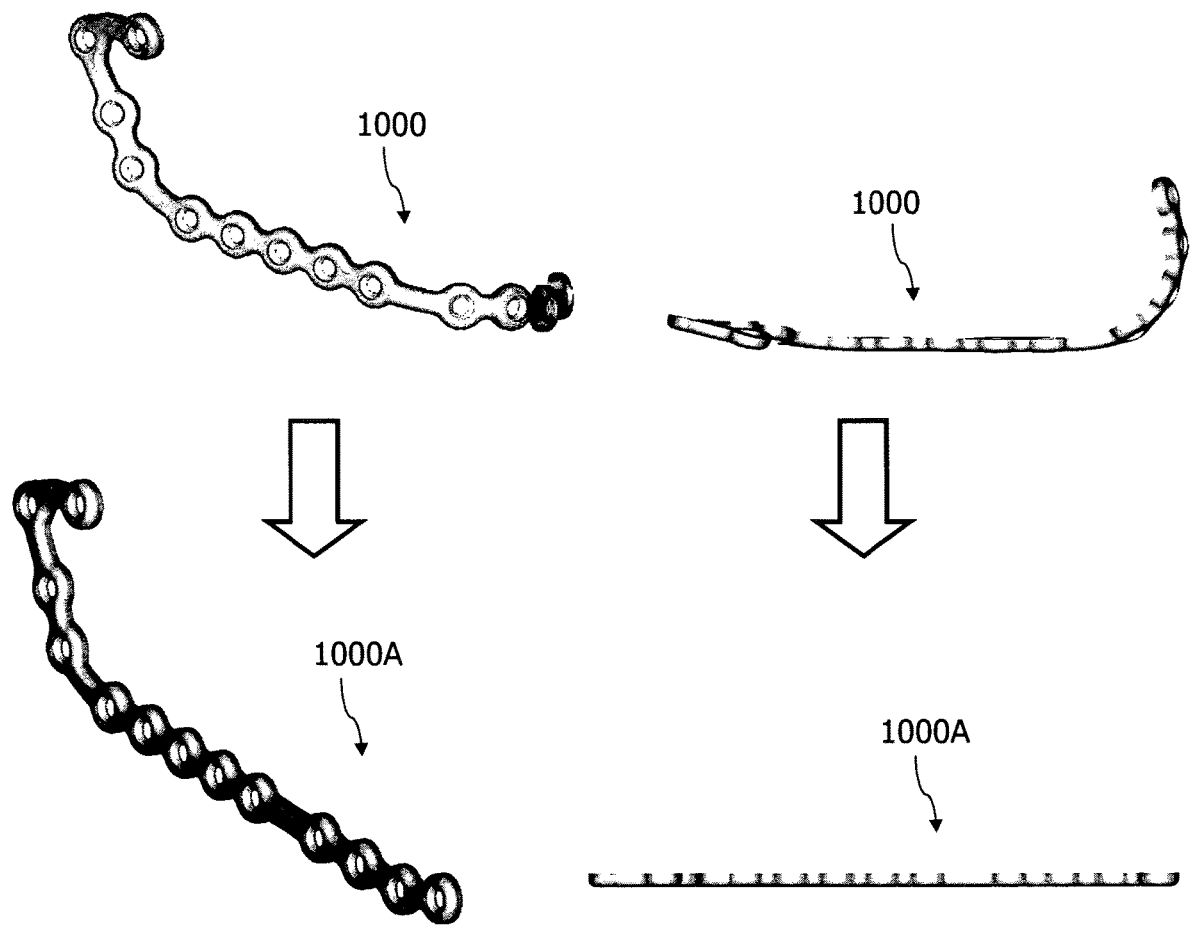
FIG. 16 is a schematic diagram graphically illustrating the transition from a non-planar bone plate to an unfolded state of that bone plate.

With reference to step 15 of the flow diagram 300 of FIG. 4, the virtually reconstructed portion 1400 of the bone 410 may be scaled down (and/or offset) so that the geometric data defining the bone plate design (and the bone plate 1000 itself) define an offset into the bone gap 460 as illustrated in FIGS. 15 and 16.

Figure 19:
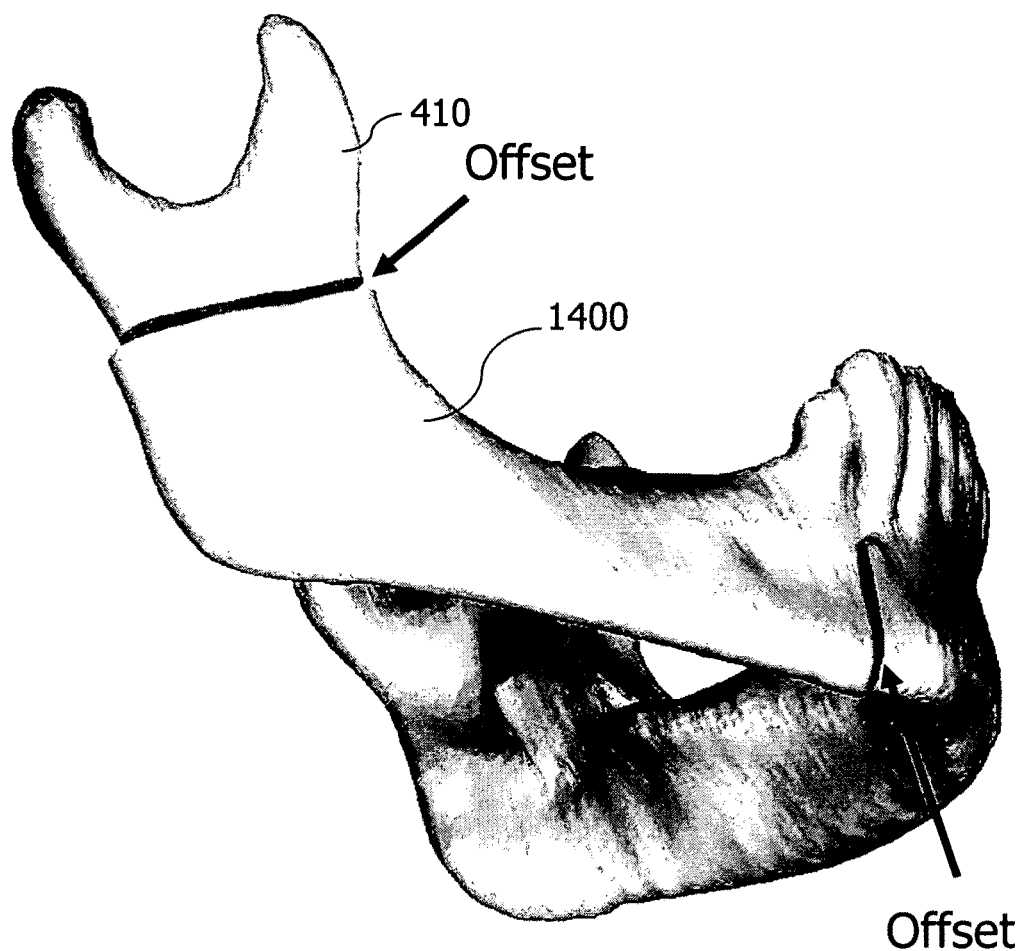
FIG. 19 is a schematic diagram illustrating a model of a bone in which a bone portion is offset.

The resulting offset of the bone plate 1000 in the medial direction provides more space between the bone plate 1000 and tissue covering the bone plate 1000. As shown in FIG. 19, the offset may be configured such that the plate portion 1600 extending over the bone gap 460 is offset, relative to the plate portion 1610 adjacent to the bone gap 460, into the bone gap 460. The offset will typically amount to 0.3 to 5 mm. In one embodiment, the offset may approximately correspond to a thickness of the plate 1000 in a region of the bone gap 460 (of, e.g., 2.0 or 2.8 mm).

Figure 20:
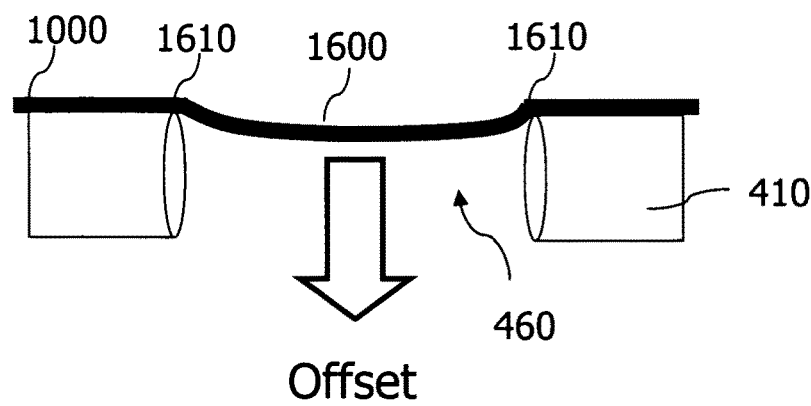
FIG. 20 schematically illustrates the offset of FIG. 13 with respect to a bone plate.

Since the data set geometrically defining the bone plate design is generated (also) based on the reconstruction data, the artificially introduced offset of the reconstruction data with respect to the shape data as visualized in FIG. 20 (also) influences the generation of that data set and thus the form of the actual bone plate 1000 resulting from the manufacturing process that is based on that data set. It will be appreciated that a reconstruction plate 100 with an offset in a region of a bone gap can also be defined and manufactured using operations different from those described above. For this reason, any bone plate with a plate portion intended to cover a bone gap may be provided with an offset as described herein.

The computing system 100 will typically be operated by manufacturing personel of a bone plate manufacturer. If desired, a surgeon may assist the bone plate design operation on the display device 120 (e.g., via a web conference across the computer network 160 of FIG. 1). The plate design functionality may provide error messages upon violating predefined plate geometry rules during the customization process. As an example, error messages may be created if a fixation opening 710 is placed close to the resection planes 440, 450 or if a predefined minimum number of fixation openings 710 (e.g., per bone segment) has not been defined.

In sum, the bone plate design approach discussed herein provides additional design operations that can be performed prior to manufacturing the bone plate. As such, the customization operations in the operating room can be reduced to an absolute minimum, and the operating room time can thus be reduced. Moreover, the possibility of a patient-specific placement of fixation openings and the patient-specific definition of other geometric design features ensures that the implantation of the plate causes minimum pain to the patient while at the same time providing maximum plate stability where needed.

In the foregoing principles, embodiments and various modes of implementing the technique disclosed herein have exemplarily been described. The present invention should not be construed as being limited to the particular principles, embodiments and mode discussed herein. Rather, it will be appreciated that various changes and modifications may be made by a person skilled in the art without departing from the scope of the present invention as defined in the claims that follow.

The invention claimed is:

1. A computer-implemented method of generating a data set that geometrically defines a bone plate design for a bone plate with at least a first fixation opening and a second fixation opening being configured to receive fixation members for fixing the bone plate to bone and at least one plate segment, the method comprising:

visualizing, based on shape data of the bone, a virtual bone model on a display device;

deriving plate design data representative of a plate-specific design property, wherein deriving the plate design data comprises:

selecting a first point and a second point on the virtual bone model, the first point being representative of a center position of the first fixation opening and the second point being representative of a center position of the second fixation opening, the second point being spaced from the first point; and creating a curve based on the first point and the second point, the curve interconnecting the first point and the second point and being representative of a length of the at least one plate segment of the bone plate design; and generating a data set that geometrically defines the bone plate design from at least the plate design data and one or more generic plate parameters, the generic plate parameters being selected from a group consisting of a number of the fixation openings of the bone plate, a geometric property of the fixation openings, a number of the segments of the bone plate, a geometric property of the at least one segment of the bone plate, at least one of a local and a total thickness of the bone plate, at least one of a local and a total width of the bone plate, and at least one of a local and a total length of the bone plate.

2. The method of claim 1, wherein the first point and the second point are derived to lie on a bone surface defined by the virtual bone model.

3. The method of claim 1, further comprising visualizing, on the display device, the first point and the second point relative to the virtual bone model.

4. The method of claim 3, further comprising visualizing, on the display device, a manipulation of the points, and further comprising adapting the plate design data in accordance with the manipulation.

5. The method of claim 4, wherein the manipulation comprises at least one of a deletion, insertion and shifting of one of the first point and the second point.

6. The method of one of claim 5, wherein the step of determining the curve is further representative of an extension of the bone plate.

7. The method of one of claim 6, further comprising visualizing the curve on the display device.

8. The method of claim 7, further comprising adapting the visualized curve responsive to the manipulation of the first point and the second point.

9. The method of claim 1, wherein at least one of the plate design data and the data set geometrically defining the bone plate design are derived or generated based on the shape data.

10. The method of claim 9, further comprising analyzing the shape data to define at least one of an out-of-plane bending and a torsion of the bone plate.

11. The method of claim 1, wherein the method further comprises providing a software-based parameter editing function configured to permit editing of the one or more geometric plate parameters.

12. The method of claim 1, further comprising visualizing a virtual plate model based on the plate design data.

13. The method of claim 1, wherein the bone comprises at least one bone portion that is missing or to be removed and wherein the bone plate is adapted to extend at least partially over a bone gap previously filled by the bone portion that is missing or to be removed.

14. The method of claim 13, further comprising generating reconstruction data for the bone portion that is missing or to be removed, and wherein the data set that geometrically defines the bone plate design is further generated from the reconstruction data.

15. The method of claim 13, further comprising generating the data set that geometrically defines the bone plate design such that a first plate portion extending over the bone gap is offset, relative to a section of a second plate portion adjacent to the bone gap, into the bone gap.

16. The method of claim 1, wherein the data set geometrically defines the design of a craniofacial bone plate.

17. A device for designing a bone plate with at least a first fixation opening and a second fixation opening configured to receive fixation members for fixing the bone plate to bone and at least one plate segment, the device comprising:

a display device adapted to visualize, based on shape data of the bone, a virtual bone model and to display a pointer relative to the virtual bone model, the pointer being positionable relative to the virtual bone model by user interaction; and at least one processor adapted to derive plate design data representative of a plate-specific design property from relationships between the pointer and the virtual bone model, wherein deriving the plate design data comprises:

selecting a first point and a second point on the virtual bone model using the pointer, the first point being representative of a center position of the first fixation opening and the second point being representative of a center position of the second fixation opening, the second point being spaced from the first point; and creating a curve based on the first point and the second point, the curve interconnecting the first point and the second point and being representative of a length of the at least one plate segment of the plate design, wherein the at least one processor is adapted to generate a data set that geometrically defines a bone plate design from at least the plate design data and one or more generic plate parameters, the generic plate parameters being selected from the group consisting of a number of the fixation openings of the bone plate, a geometric property of the fixation openings, a number of the segments of the bone plate, a geometric property of the at least one segment of the bone plate, at least one of a local and a total thickness of the bone plate, at least one of a local and a total width of the bone plate, and at least one of a local and a total length of the bone plate.

18. The device of claim 17, wherein the curve is further representative of an extension of the bone plate.

* * * * *